US011771659B2

(12) United States Patent
Hazen et al.

(10) Patent No.: US 11,771,659 B2
(45) Date of Patent: *Oct. 3, 2023

(54) TREATING DISEASE AND PROMOTING WEIGHT LOSS BY INHIBITING THE TMA/FMO3/TMAO PATHWAY

(71) Applicant: The Cleveland Clinic Foundation, Cleveland, OH (US)

(72) Inventors: Stanley L. Hazen, Pepper Pike, OH (US); Jonathan Mark Brown, Cleveland, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 502 days.

This patent is subject to a terminal disclaimer.

(21) Appl. No.: 16/624,389

(22) PCT Filed: Jun. 19, 2018

(86) PCT No.: PCT/US2018/038322
§ 371 (c)(1),
(2) Date: Dec. 19, 2019

(87) PCT Pub. No.: WO2018/236899
PCT Pub. Date: Dec. 27, 2018

(65) Prior Publication Data
US 2020/0121615 A1 Apr. 23, 2020

Related U.S. Application Data

(60) Provisional application No. 62/521,872, filed on Jun. 19, 2017.

(51) Int. Cl.
| | |
|---|---|
| *A61K 31/045* | (2006.01) |
| *A61P 3/04* | (2006.01) |
| *A61K 31/133* | (2006.01) |
| *A61K 31/14* | (2006.01) |
| *A61K 31/205* | (2006.01) |
| *A61K 31/4164* | (2006.01) |
| *A61K 31/5375* | (2006.01) |
| *A61K 31/616* | (2006.01) |
| *A61K 31/675* | (2006.01) |
| *A61K 31/688* | (2006.01) |
| *A61K 31/7036* | (2006.01) |
| *A61K 31/7105* | (2006.01) |
| *A61K 45/06* | (2006.01) |
| *A61K 35/741* | (2015.01) |

(52) U.S. Cl.
CPC .......... *A61K 31/045* (2013.01); *A61K 31/133* (2013.01); *A61K 31/14* (2013.01); *A61K 31/205* (2013.01); *A61K 31/4164* (2013.01); *A61K 31/5375* (2013.01); *A61K 31/616* (2013.01); *A61K 31/675* (2013.01); *A61K 31/688* (2013.01); *A61K 31/7036* (2013.01); *A61K 31/7105* (2013.01); *A61K 35/741* (2013.01); *A61P 3/04* (2018.01); *A61K 45/06* (2013.01)

(58) Field of Classification Search
None
See application file for complete search history.

(56) References Cited

U.S. PATENT DOCUMENTS

| 4,525,156 | A | * | 6/1985 | Benusa | ............... A61M 1/0058 604/28 |
|---|---|---|---|---|---|
| 5,223,409 | A | | 6/1993 | Ladner et al. | |
| 6,015,577 | A | * | 1/2000 | Eisert | ..................... A61K 9/209 424/451 |
| 9,694,020 | B2 | * | 7/2017 | Hazen | ..................... A61K 31/43 |
| 10,117,879 | B2 | * | 11/2018 | Hazen | ..................... A61P 13/12 |
| 10,241,093 | B2 | * | 3/2019 | Hazen | ..................... C12Q 1/18 |
| 10,933,072 | B2 | * | 3/2021 | Hazen | ..................... A61K 31/13 |
| 10,983,100 | B2 | * | 4/2021 | Hazen | ................ A61K 31/4164 |
| 11,331,280 | B2 | * | 5/2022 | Hazen | ..................... A61K 31/10 |
| 2012/0157397 | A1 | | 6/2012 | Hazen et al. | |
| 2012/0207822 | A1 | | 8/2012 | Hazen et al. | |
| 2016/0074440 | A1 | | 3/2016 | Brugere et al. | |
| 2016/0089387 | A1 | | 3/2016 | Hazen | |
| 2017/0151208 | A1 | * | 6/2017 | Hazen | ..................... A61K 31/22 |
| 2021/0038550 | A1 | * | 2/2021 | Hazen | ....................... A61P 9/04 |

OTHER PUBLICATIONS

"Atherosclerotic aneurysm." Farlex Partner Medical Dictionary. 2012. (Retrieved: Sep. 11, 2021) https://medical-dictionary.thefreedictionary.com/atherosclerotic+aneurysm. (Year: 2012).*
Bieze et al., "Diagnostic Accuracy of 18F-Methylcholine Positron Emission Tomography/Computed Tomography for Intra- and Extrahepatic Hepatocellular Carcinoma", 2014, Hepatology, 59(3), pp. 996-1006. (Year: 2014).*
Paul et al., "Diet-induced changes in maternal gut microbiota and metabolomic profiles influence programming of offspring obesity risk in rats", 2016, Scientific Reports, vol. 6, Article No. 20683, pp. 1-14. (https://doi.org/10.1038/srep20683) (Year: 2016).*
International Search Report and Written Opinion for PCT/US18/38322, dated Sep. 10, 2018, 8 pages.
Extended European Search Report for PCT/US2018038322, dated Feb. 9, 2021. 10 pages.
Morris, Link between the gut and adipose tissues. Nature reviews. Endocrinology, vol. 13, No. 9, Jul. 7, 2017(Jul. 7, 2017) pp. 501-501.
Ausubel et al., eds. Current Protocols in Molecular Biology 1999, J. Wiley: New York.
Bäckhed, et al., The gut microbiota as an environmental factor that regulates fat storage. Proc Natl Acad Sci U S A. Nov. 2, 2004;101(44):15718-23.

(Continued)

*Primary Examiner* — My-Chau T. Tran
(74) *Attorney, Agent, or Firm* — CASIMIR JONES, S.C.; Jason R. Bond

(57) ABSTRACT

Provided herein are compositions, systems, and methods for causing weight loss and treating and/or preventing a disease or condition, such as obesity, diabetes, and cancer, with an agent or procedure that inhibits the TMA/FMO3/TMAO pathway in a subject.

20 Claims, 20 Drawing Sheets

Specification includes a Sequence Listing.

(56) References Cited

OTHER PUBLICATIONS

Bartelt et al., Adipose tissue browning and metabolic health. Nat Rev Endocrinol. Jan. 2014;10(1):24-36.
Bennett et al., Trimethylamine-N-oxide, a metabolite associated with atherosclerosis, exhibits complex genetic and dietary regulation. Cell Metab 2013: 17, 49-60.
Brown et al., The gut microbial endocrine organ: bacterially derived signals driving cardiometabolic diseases. Annu Rev Med. 2015;66:343-59.
Carell et al., Angew. Chem. Int. Ed. Engl. 1994: 33:2061.
Carell et al., Angew. Chem. Int. Ed. Engl. 1994: 33.2059.
Cashman et al., Human flavin-containing monooxygenases. Annu Rev Pharmacol Toxicol. 2006;46:65-100.
Cho et al., an Unnatural Biopolymer. Science 1993: 261:1303.
Cichero et al., a homology modelling-driven study leading to the discovery of the first mouse trace amine-associated receptor 5 (TAAR5) antagonists. MedChemComm, 2016: 7(2), 353-364.
Civelek et al., Genetic Regulation of Adipose Gene Expression and Cardio-Metabolic Traits. Am J Hum Genet. Mar. 2, 2017;100(3):428-443.
Cox et al., Altering the intestinal microbiota during a critical developmental window has lasting metabolic consequences. Cell. Aug. 14, 2014;158(4):705-721.
Cull et al., Screening for receptor ligands using large libraries of peptides linked of the C terminus of the lac repressor. Proc. Nad. Acad. Sci. USA 1992: 89:18651869.
Cwirla et al., Peptides on phage: A vast library of peptides for identifying ligands. Proc. Natl. Acad. Sci. 1990: 87:6378-6382.
Dambrova et al., Diabetes is Associated with Higher Trimethylamine N-oxide Plasma Levels. Exp Clin Endocrinol Diabetes. Apr. 2016;124(4):251-6.
Das et al., Integrative network analysis reveals different pathophysiological mechanisms of insulin resistance among Caucasians and African Americans. BMC Med Genomics. Feb. 7, 2015;8:4.
Devlin et al., Random peptide libraries: A source of specific protein binding molecules. Science 1990: 249:404-406.
Dewitt et al., "Diversomers": An approach to nonpeptide, nonoligomeric chemical diversity. Proc. Natl. Acad. Sci. U.S.A. 1993: 90:6909.
Erb et al., Recursive deconvolution of combinatorial chemical libraries. Proc. Nad. Acad. Sci. 1994: USA 91:11422.
Felici et al., Selection of antibody ligands from a large library of oligopeptides expressed on multivalent exposition vector. J. Mol. Biol. 1991: 222:301.
Fodor et al., Multiplexed biochemical assays with biological chips. Nature 1993: 364:555-556.
Gallop et al., Applications of combinatorial technologies to drug discovery. J. Med. Chem. 1994: 37:1233.
Gao et al., Dietary trimethylamine N-oxide exacerbates impaired glucose tolerance in mice fed a high fat diet. J Biosci Bioeng. Oct. 2014;118(4):476-81.
Gregory et al., Transmission of atherosclerosis susceptibility with gut microbial transplantation. J Biol Chem. Feb. 27, 2015;290(9):5647-60.
Hage et al., Recent advances in chromatographic and electrophoretic methods for the study of drug-protein interactions. J Chromatogr B Biomed Sci Appl. Oct. 10, 1997;699(1-2):499-525.
Heegaard, Capillary electrophoresis for the study of affinity interactions. J Mol Recognit. Winter 1998;11(1-6):141-8.
Jiang et al., Maternal choline intake alters the epigenetic state of fetal cortisol-regulating genes in humans. FASEB J. Aug. 2012;26(8):3563-74.
Koeth et al., Intestinal microbiota metabolism of L-carnitine, a nutrient in red meat, promotes atherosclerosis. Nat Med 2013: 19, 576-585.
Koeth et al. γ-Butyrobetaine is a proatherogenic intermediate in gut microbial metabolism of L-carnitine to TMAO. Cell Metab 2014: 20, 799-812.
Lam. Application of combinatorial library methods in cancer research and drug discovery.Anticancer Drug Des. 1997: 12:145.
Lam. A new type of synthetic peptide library for identifying ligand-binding activity. Nature 1991: 354:82-84.
Lever et al., Betaine and Trimethylamine-N-Oxide as Predictors of Cardiovascular Outcomes Show Different Patterns in Diabetes Mellitus: An Observational Study. PLoS One. Dec. 10, 2014;9(12):e114969.
Ley et al., Obesity alters gut microbial ecology. Proc Natl Acad Sci U S A. Aug. 2, 2005;102(31):11070-5.
Li et al., Synchronous evolution of an odor biosynthesis pathway and behavioral response. Curr Biol. Jan. 7, 2013;23(1):11-20.
Mafune et al., Associations among serum trimethylamine-N-oxide (TMAO) levels, kidney function and infarcted coronary artery number in patients undergoing cardiovascular surgery: a cross-sectional study. Clin Exp Nephrol. Oct. 2016;20(5):731-739.
Matsuda et al., Insulin sensitivity indices obtained from oral glucose tolerance testing: comparison with the euglycemic insulin clamp. Diabetes Care. Sep. 1999;22(9):1462-70.
Miao et al., Flavin-containing monooxygenase 3 as a potential player in diabetes-associated atherosclerosis. Nat Commun. Apr. 7, 2015;6:6498.
Missailidis et al., Serum Trimethylamine-N-Oxide Is Strongly Related to Renal Function and Predicts Outcome in Chronic Kidney Disease. PLoS One. Jan. 11, 2016;11(1):e0141738.
Muoio, Metabolic inflexibility: when mitochondrial indecision leads to metabolic gridlock. Cell. Dec. 4, 2014;159(6):1253-62.
Parks et al., Genetic control of obesity and gut microbiota composition in response to high-fat, high-sucrose diet in mice. Cell Metab. Jan. 8, 2013;17(1):141-52.
Poly et al., The relation of dietary choline to cognitive performance and white-matter hyperintensity in the Framingham Offspring Cohort. Am J Clin Nutr. Dec. 2011;94(6):1584-91.
Puigserver et al;, A cold-inducible coactivator of nuclear receptors linked to adaptive thermogenesis. Cell. Mar. 20, 1998;92(6):829-39.
Schugar et al., The TMAO-Producing Enzyme Flavin-Containing Monooxygenase 3 regulates obesity and the beiging of white adipose tissue, Cell Reports, vol. 19, No. 12, Jun. 20, 2017(Jun. 20, 2017) pp. 2451-2461.
Romano et al., Intestinal microbiota composition modulates choline bioavailability from diet and accumulation of the proatherogenic metabolite trimethylamine-N-oxide. mBio. Mar. 17, 2015;6(2):e02481.
Scott et al., Searching for peptide ligands with an epitope library. Science 1990: 249:386-390.
Sharma et al., Tissue-Specific and Genetic Regulation of Insulin Sensitivity-Associated Transcripts in African Americans. J Clin Endocrinol Metab. Apr. 2016;101(4):1455-68.
Shaw et al., Choline and risk of neural tube defects in a folate-fortified population. Epidemiology. Sep. 2009;20(5):714-9.
Shih et al., Flavin containing monooxygenase 3 exerts broad effects on glucose and lipid metabolism and atherosclerosis. J Lipid Res. Jan. 2015;56(1):22-37.
Stancakova et al., Association of 18 confirmed susceptibility loci for type 2 diabetes with indices of insulin release, proinsulin conversion, and insulin sensitivity in 5,327 nondiabetic Finnish men. Diabetes. Sep. 2009;58(9):2129-36.
Suzuki et al.,Trimethylamine N-oxide and prognosis in acute heart failure. Heart. Jun. 1, 2016;102(11):841-8.
Tang et al., Intestinal microbial metabolism of phosphatidylcholine and cardiovascular risk. N Engl J Med. Apr. 25, 2013;368(17):1575-84.
Tang et al., Prognostic value of elevated levels of intestinal microbe-generated metabolite trimethylamine-N-oxide in patients with heart failure: refining the gut hypothesis. J Am Coll Cardiol. 2014: 64, 1908-1914.
Tang et al., Increased Trimethylamine N-Oxide Portends High Mortality Risk Independent of Glycemic Control in Patients with Type 2 Diabetes Mellitus. Clin Chem. Jan. 2017;63(1):297-306.
Thomas et al., The serine hydrolase ABHD6 Is a critical regulator of the metabolic syndrome. Cell Rep. Oct. 31, 2013;5(2):508-20.
Trøseid et al., Microbiota-dependent metabolite trimethylamine-N-oxide is associated with disease severity and survival of patients with chronic heart failure. J Intern Med. Jun. 2015;277(6):717-26.
Turnbaugh et al., the core gut microbiome, energy balance and obesity. J Physiol. Sep. 1, 2009;587(Pt 17):4153-8.

(56) References Cited

OTHER PUBLICATIONS

Ussar et al., ASC-1, PAT2, and P2RX5 are cell surface markers for white, beige, and brown adipocytes. Sci Transl Med. Jul. 30, 2014;6(247):247ra103.

Wang et al., Gut flora metabolism of phosphatidylcholine promotes cardiovascular disease. Nature 2011: 472, 57-63.

Wang et al., Prognostic value of choline and betaine depends on intestinal microbiota-generated metabolite trimethylamine-N-oxide. Eur Heart J. Apr. 2014;35(14):904-10.

Wang et al., Non-lethal Inhibition of Gut Microbial Trimethylamine Production for the Treatment of Atherosclerosis. Cell. Dec. 17, 2015;163(7):1585-95.

Warrier et al., The TMAO-Generating Enzyme Flavin Monooxygenase 3 Is a Central Regulator of Cholesterol Balance. Cell Rep. Jan. 20, 2015;10(3):326-338.

Wu et al., Beige adipocytes are a distinct type of thermogenic fat cell in mouse and human. Cell. Jul. 20, 2012;150(2):366-76.

Zhu et al., Gut Microbial Metabolite TMAO Enhances Platelet Hyperreactivity and Thrombosis Risk. Cell. Mar. 24, 2016;165(1):111-124.

Zuckermann et al., Discovery of nanomolar ligands for 7-transmembrance g-protein-coupled receptors from a diverse N-(substituted)glycine Peptoid library J. Med. Chem. 1994: 37: 2678-85.

Houghten et al., The use of synthetic peptide combinatorial libraries for the indentification of bioactive peptides. Biotechniques. 1992: 13:412-421.

\* cited by examiner

FIG. 2
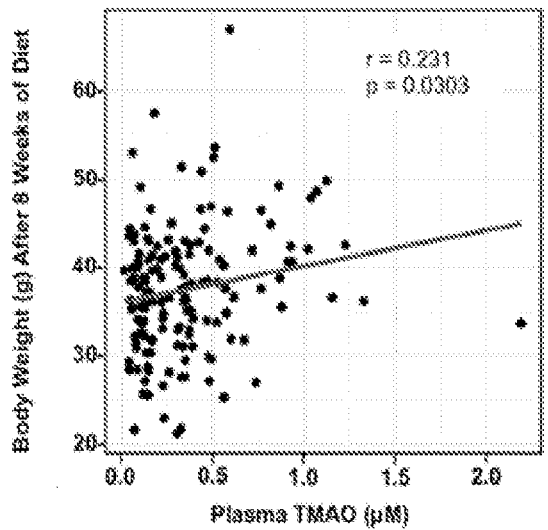
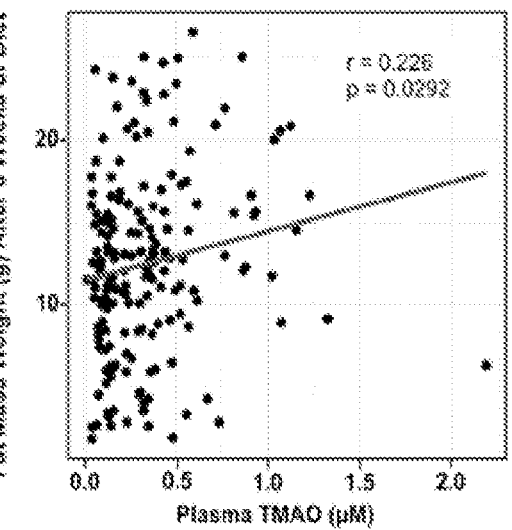
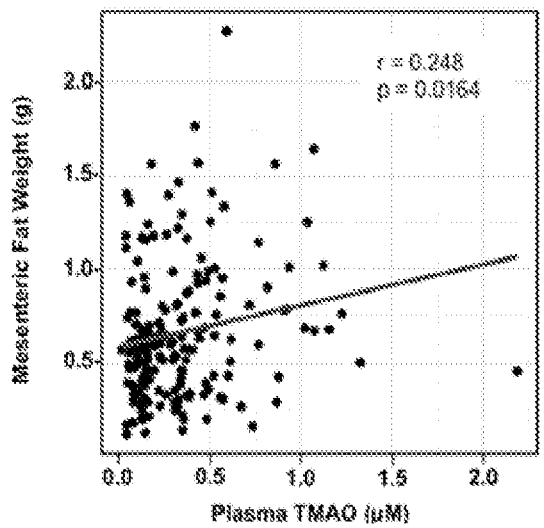
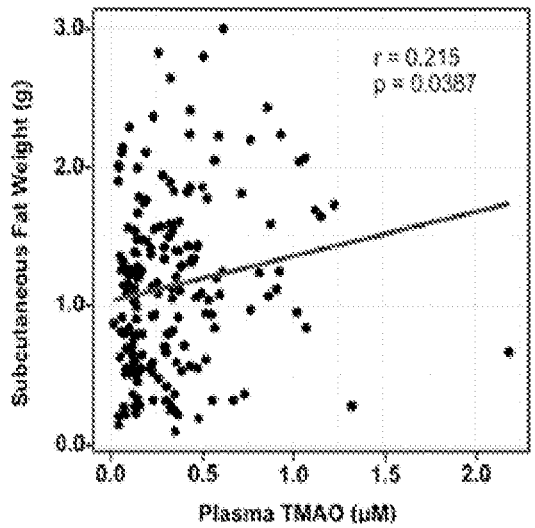

FIG. 2 (cont.)

E  Association Between WAT *FMO3* Expression and Metabolic Traits or Beige Adipocyte Marker Genes in 770 men

| | Metabolic Traits | | | | | | | Brown/Beige Adipocyte Marker Genes | | | | | | | | | |
|---|---|---|---|---|---|---|---|---|---|---|---|---|---|---|---|---|---|
| | Body Mass Index | | Waist-to-hip ratio | | Basal lipolysis | | *PRDM16* rs12409277 | | *PPARG* rs1175544 | | *PGC1a* rs11777927 | | *UCP1* rs1800592 | | *TBX1* rs11178527 | |
| | r | p | r | p | r | p | r | p | r | p | r | p | r | p | r | p |
| *FMO3* | 0.293 | 6.1E-11 | 0.185 | 2.3E-07 | -0.110 | 2.3E-03 | -0.124 | 5.8E-04 | -0.229 | 1.3E-10 | -0.177 | 8.2E-07 | -0.161 | 7.6E-06 | -0.131 | 2.7E-04 |

A   CRISPR-Cas9 Strategy

5'-GACCATATAGAAGAGGGCAGGGCCAGCATTTACCAA

TCGGTCTTCACCAACTCTTCCAAAGAGATGATGTGT

TTCCAGACTTCCCCTATCCCGATGACTTTCCCAACT
            3'-GATAGGGCTACTGAAAGGGT-5'

TCATGCATCACAGCAAGCTCCAAGAATACATCACTT

CATTTGCCAAGGAAAAGAACCTCCTGAAATACATAC

AGTTTGAG-3'

FIG. 4 yeaW

GeneID|6060925|ref|NC_010473.1|1973260-1974384 Escherichia coli str. K-12 substr. DH10B (SEQ ID NO:3)

ATGAGCAATCTGAGCCCTGACTTTGTACTACCCGAAAATTTTTGCGCTAACCCGCAAGAGGCGTGGACCA
TTCCTGCCCGTTTTTATACCGATCAGAACGCGTTTGAACACGAAAAGAGAACGTCTTCGCCAAAAGCTG
GATTTGCGTCGCTCACAGCAGCGAACTGGCGAATGCCAATGATTATGTGACGCGTGAGATCATTGGCGAA
AGCATCGTGCTGGTACGCGGTCGTGATAAGGTTTTGCGCGCGTTCTATAACGTGTGTCCGCACCGTGGTC
ATCAGTTGTTGAGCGGTGAAGGAAAAGCAAAAAATGTGATTACCTGCCCGTATCACGCATGGGCATTCAA
ACTCGATGGCAACCTGGCCCATGCACGTAACTGCGAAAACGTCGCCAATTTCGATAGCGACAAAGCGCAA
CTGGTTCCGGTGCGTCTGGAAGAATATGCCGGATTCGTCTTCATCAACATGGACCCCAACGCCACCAGCG
TAGAAGATCAATTACCCGGCCTGGGCGCGAAAGTGCTGGAAGCCTGCCCGGAAGTCCACGATCTGAAACT
GGCGGCCCGCTTTACCACCCGCACGCCTGCCAACTGGAAGAACATTGTCGATAACTATCTCGAGTGCTAT
CACTGTGGTCCGGCGCATCCAGGTTTCTCCGACTCCGTACAGGTTGATCGTTACTGGCACACCATGCACG
GTAACTGGACGCTGCAATACGGTTTCGCCAAACCGTCCGAACAGTCGTTTAAATTTGAAGAGGGTACGGA
TGCGGCATTCCACGGTTTCTGGCTGTGGCCGTGCACGATGCTGAACGTCACCCCGATCAAAGGGATGATG
ACGGTCATTTATGAATTCCCGGTGGATTCTGAAACTACCCTGCAAAACTACGATATTTACTTCACCAATG
AAGAGTTAACCGACGAGCAAAAATCGCTGATTGAGTGGTATCGCGATGTGTTCCGTCCGGAAGATTTACG
TCTGGTTGAAAGCGTACAGAAAGGGCTGAAATCGCGTGGCTATCGTGGTCAGGGGCGCATCATGGCCGAC
AGTAGCGGTAGTGGCATTTCCGAACATGGTATCGCCCATTTCCATAATCTGCTGGCGCAGGTGTTTAAGG
ACTAA (SEQ ID NO:4)

MSNLSPDFVLPENFCANPQEAWTIPARFYTDQNAFEHEKENVFAKSWICVAHSSELANANDYVTREIIGE
SIVLVRGRDKVLRAFYNVCPHRGHQLLSGEGKAKNVITCPYHAWAFKLDGNLAHARNCENVANFDSDKAQ
LVPVRLEEYAGFVFINMDPNATSVEDQLPGLGAKVLEACPEVHDLKLAARFTTRTPANWKNIVDNYLECY
HCGPAHPGFSDSVQVDRYWHTMHGNWTLQYGFAKPSEQSFKFEEGTDAAFHGFWLWPCTMLNVTPIKGMM
TVIYEFPVDSETTLQNYDIYFTNEELTDEQKSLIEWYRDVFRPEDLRLVESVQKGLKSRGYRGQGRIMAD
SSGSGISEHGIAHFHNLLAQVFKD

FIG. 5 yeaX

GeneID|6060982|ref|NC_010473.1|1974440-1975405 Escherichia coli str. K-12 substr. DH10B (SEQ ID NO:5)

ATGTCAGACTATCAAATGTTTGAAGTACAGGTGAGCCAGGTTGAACCCCTTACCGAACAGGTGAAACGCT
TCACGCTGGTGGCAACCGATGGCAAACCATTACCTGCGTTTACCGGAGGAAGTCACGTCATTGTGCAGAT
GAGCGATGGTGATAACCAGTACAGCAATGCGTATTCACTACTGAGTTCGCCGCATGACACCTCTTGTTAT
CAGATTGCCGTTCGGCTGGAGGAAAACTCGCGCGGCGGTTCCCGCTTTTTGCATCAGCAGGTAAAAGTGG
GCGATCGGTTAACGATTTCAACGCCTAATAACCTGTTTGCGCTAATTCCCTCAGCCAGAAAGCATCTGTT
TATCGCGGGCGGTATTGGTATCACCCCTTTCCTGTCGCACATGGCAGAGCTGCAACACAGCGACGTCGAC
TGGCAGCTACATTACTGCTCGCGAAATCCAGAAAGTTGCGCATTTCGTGATGAGCTAGTCCAGCATCCGC
AGGCTGAGAAAGTCCATTTGCATCATTCATCAACCGGAACACGACTGGAATTAGCGCGATTATTGGCGGA
TATCGAACCTGGCACACACGTTTATACCTGTGGCCCCGAGGCGCTAATTGAAGCGGTAAGAAGTGAAGCT
GCGCGTCTGGACATCGCCGCCGATACGCTGCACTTTGAGCAATTTGCTATCGAAGACAAAACCGGCGATG
CATTTACCCTGGTGCTTGCCCGTTCCGGAAAAGAGTTTGTGGTGCCGGAAGAGATGACTATTTTGCAGGT
TATTGAAAATAATAAAGCCGCGAAAGTGGAATGTTTATGTCGTGAAGGGGTATGCGGAACCTGCGAAACA
GCAATACTGGAAGGTGAAGCTGACCATCGGGATCAATATTTTAGCGATGAAGAGCGTGCCAGCCAGCAAA
GTATGTTGATCTGTTGTTCGCGTGCGAAGGGTAAACGCCTGGTGTTGGATTTGTAG (SEQ ID NO:6)

MSDYQMFEVQVSQVEPLTEQVKRFTLVATDGKPLPAFTGGSHVIVQMSDGDNQYSNAYSLLSSPHDTSCY
QIAVRLEENSRGGSRFLHQQVKVGDRLTISTPNNLFALIPSARKHLFIAGGIGITPFLSHMAELQHSDVD
WQLHYCSRNPESCAFRDELVQHPQAEKVHLHHSSTGTRLELARLLADIEPGTHVYTCGPEALIEAVRSEA
ARLDIAADTLHFEQFAIEDKTGDAFTLVLARSGKEFVVPEEMTILQVIENNKAAKVECLCREGVCGTCET
AILEGEADHRDQYFSDEERASQQSMLICCSRAKGKRLVLDL

FIG. 8 (cont.)
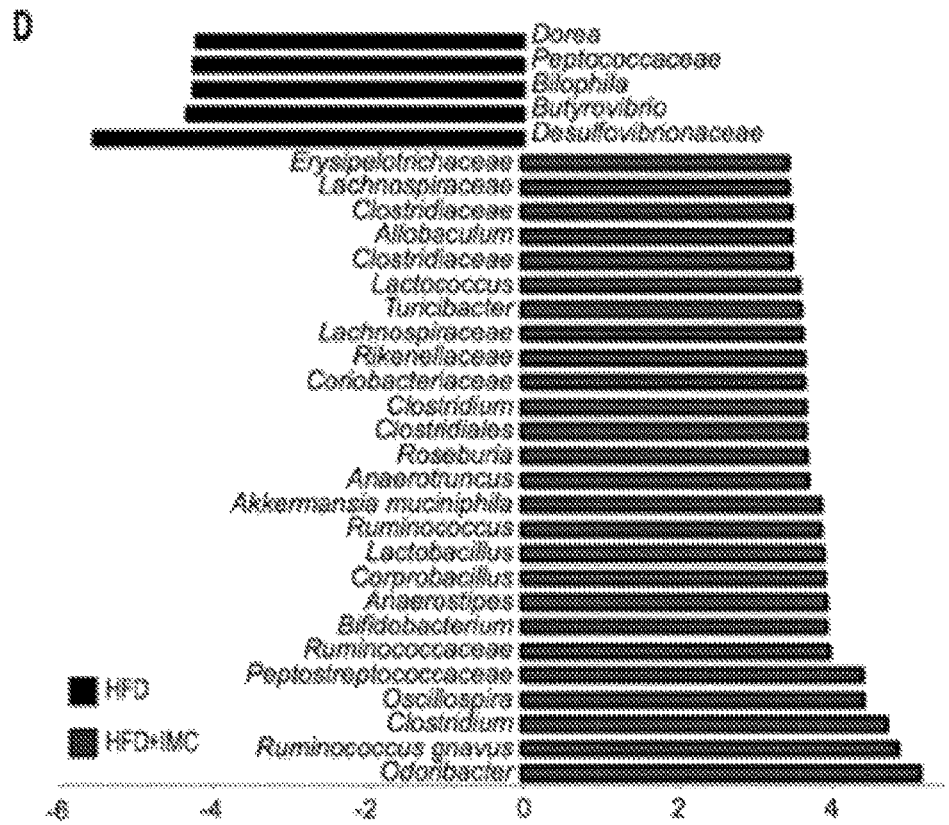
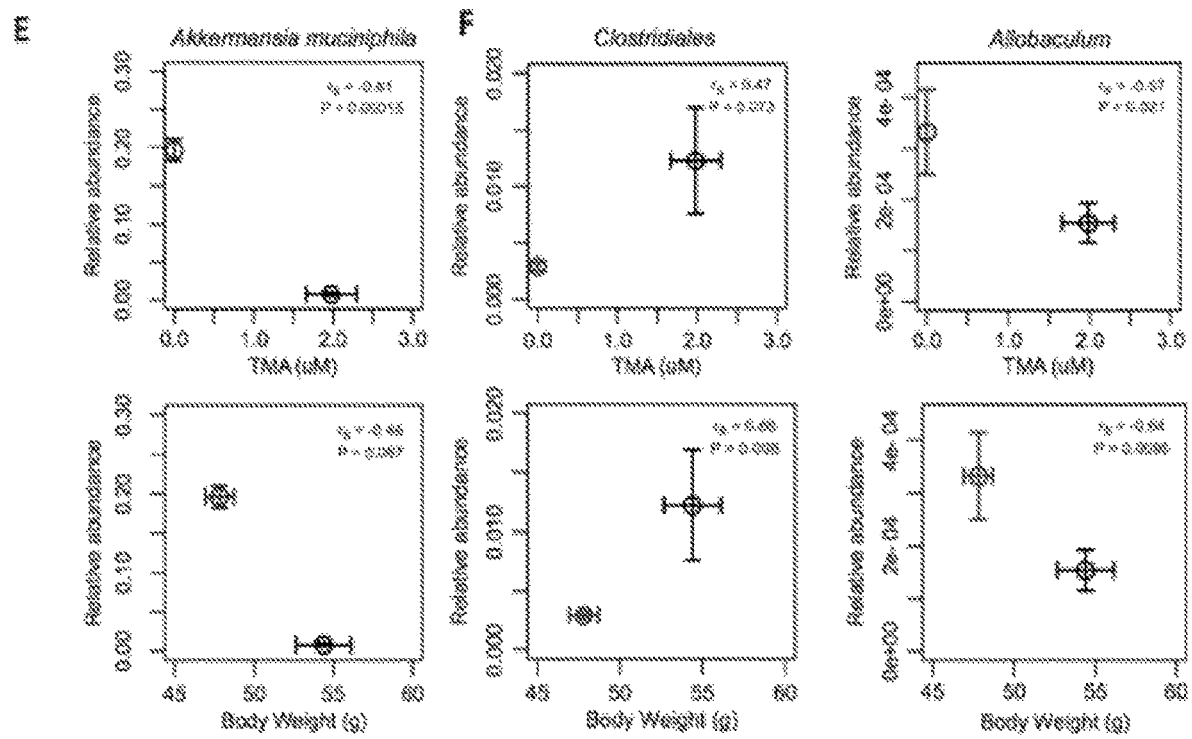

FIG. 8 (cont.)
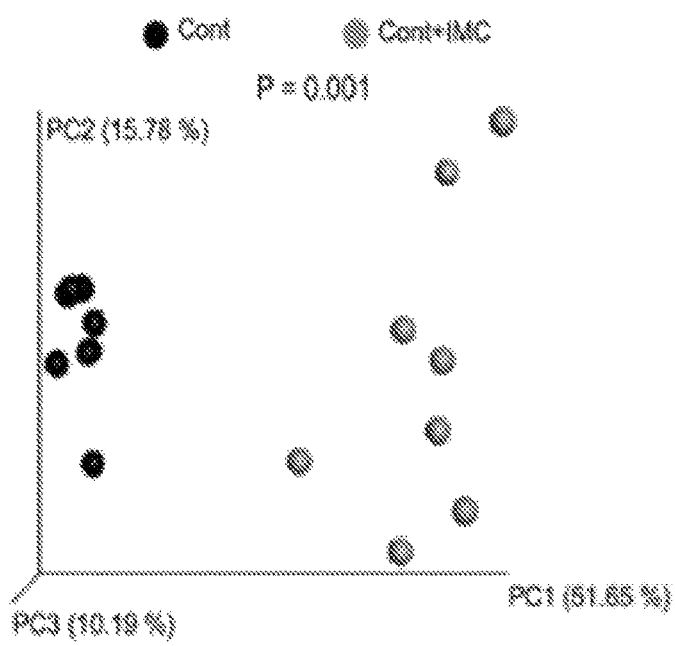
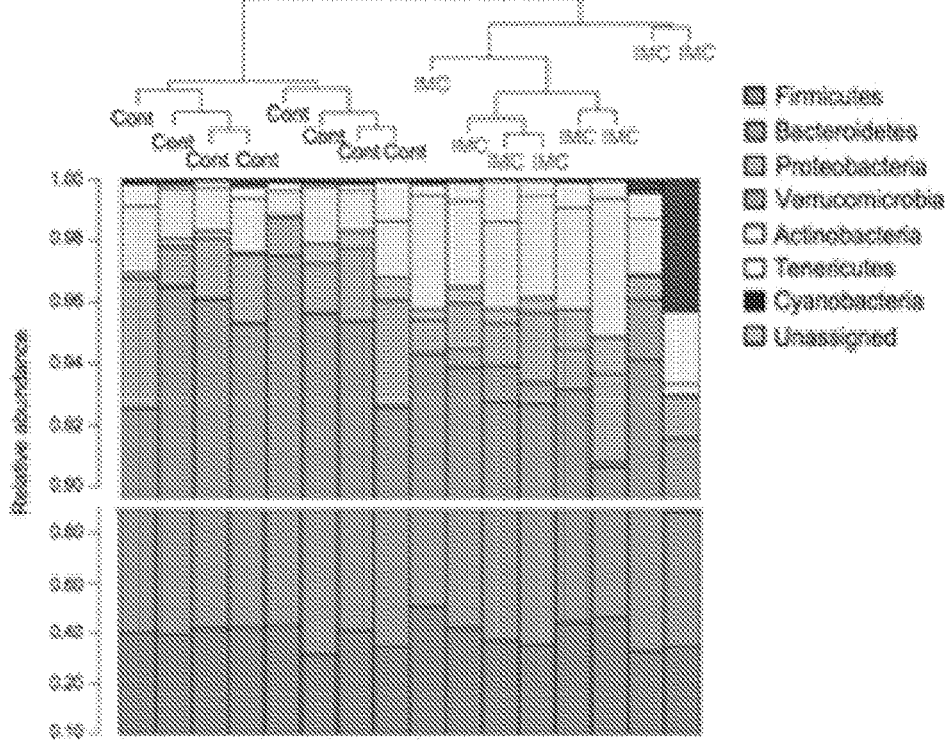

```
                         SEQUENCE LISTING

<160> NUMBER OF SEQ ID NOS: 7

<210> SEQ ID NO 1
<211> LENGTH: 188
<212> TYPE: DNA
<213> ORGANISM: Artificial sequence
<220> FEATURE:
<223> OTHER INFORMATION: Synthetic

<400> SEQUENCE: 1
gaccatatag aagagggcag ggccagcatt taccaatcgg tcttcaccaa ctcttccaaa      60
gagatgatgt gtttccagac ttcccctatc ccgatgactt tcccaacttc atgcatcaca     120
gcaagctcca agaatacatc acttcatttg ccaaggaaaa gaacctcctg aaatacatac     180
agtttgag                                                              188

<210> SEQ ID NO 2
<211> LENGTH: 20
<212> TYPE: DNA
<213> ORGANISM: Artificial sequence
<220> FEATURE:
<223> OTHER INFORMATION: Synthetic

<400> SEQUENCE: 2
tgggaaagtc atcgggatag                                                  20

<210> SEQ ID NO 3
<211> LENGTH: 1125
<212> TYPE: DNA
<213> ORGANISM: Escherichia coli str. K-12 substr. DH10B

<400> SEQUENCE: 3
atgagcaatc tgagccctga ctttgtacta cccgaaaatt tttgcgctaa cccgcaagag      60
gcgtggacca ttcctgcccg tttttatacc gatcagaacg cgtttgaaca cgaaaaagag     120
aacgtcttcg ccaaaagctg gatttgcgtc gctcacagca gcgaactggc gaatgccaat     180
```

```
gattatgtga cgcgtgagat cattggcgaa agcatcgtgc tggtacgcgg tcgtgataag    240
gttttgcgcg cgttctataa cgtgtgtccg caccgtggtc atcagttgtt gagcggtgaa    300
ggaaaagcaa aaaatgtgat tacctgcccg tatcacgcat gggcattcaa actcgatggc    360
aacctggccc atgcacgtaa ctgcgaaaac gtcgccaatt tcgatagcga caaagcgcaa    420
ctggttccgg tgcgtctgga agaatatgcc ggattcgtct tcatcaacat ggaccccaac    480
gccaccagcg tagaagatca attacccggc ctgggcgcga agtgctgga agcctgcccg     540 gaagtccacg atctgaaact ggcggcccgc tttaccaccc gcacgcctgc caactggaag    600
aacattgtcg ataactatct cgagtgctat cactgtggtc cggcgcatcc aggtttctcc    660
gactccgtac aggttgatcg ttactggcac accatgcacg gtaactggac gctgcaatac    720
ggtttcgcca aaccgtccga acagtcgttt aaatttgaag agggtacgga tgcggcattc    780
cacggtttct ggctgtggcc gtgcacgatg ctgaacgtca ccccgatcaa agggatgatg    840
acggtcattt atgaattccc ggtggattct gaaactaccc tgcaaaacta cgatatttac    900
ttcaccaatg aagagttaac cgacgagcaa aaatcgctga ttgagtggta tcgcgatgtg    960
ttccgtccgg aagatttacg tctggttgaa agcgtacaga aagggctgaa atcgcgtggc   1020
tatcgtggtc aggggcgcat catggccgac agtagcggta gtggcatttc cgaacatggt   1080
atcgcccatt tccataatct gctggcgcag gtgtttaagg actaa                  1125
```

<210> SEQ ID NO 4
<211> LENGTH: 374
<212> TYPE: PRT
<213> ORGANISM: Escherichia coli str. K-12 substr. DH10B

<400> SEQUENCE: 4

```
Met Ser Asn Leu Ser Pro Asp Phe Val Leu Pro Glu Asn Phe Cys Ala
1               5                   10                  15

Asn Pro Gln Glu Ala Trp Thr Ile Pro Ala Arg Phe Tyr Thr Asp Gln
            20                  25                  30

Asn Ala Phe Glu His Glu Lys Glu Asn Val Phe Ala Lys Ser Trp Ile
        35                  40                  45

Cys Val Ala His Ser Ser Glu Leu Ala Asn Ala Asn Asp Tyr Val Thr
    50                  55                  60

Arg Glu Ile Ile Gly Glu Ser Ile Val Leu Val Arg Gly Arg Asp Lys
65                  70                  75                  80

Val Leu Arg Ala Phe Tyr Asn Val Cys Pro His Arg Gly His Gln Leu
                85                  90                  95

Leu Ser Gly Glu Gly Lys Ala Lys Asn Val Ile Thr Cys Pro Tyr His
            100                 105                 110

Ala Trp Ala Phe Lys Leu Asp Gly Asn Leu Ala His Ala Arg Asn Cys
        115                 120                 125

Glu Asn Val Ala Asn Phe Asp Ser Asp Lys Ala Gln Leu Val Pro Val
    130                 135                 140

Arg Leu Glu Glu Tyr Ala Gly Phe Val Phe Ile Asn Met Asp Pro Asn
145                 150                 155                 160

Ala Thr Ser Val Glu Asp Gln Leu Pro Gly Leu Gly Ala Lys Val Leu
                165                 170                 175

Glu Ala Cys Pro Glu Val His Asp Leu Lys Leu Ala Ala Arg Phe Thr
            180                 185                 190

Thr Arg Thr Pro Ala Asn Trp Lys Asn Ile Val Asp Asn Tyr Leu Glu
        195                 200                 205
```

Cys Tyr His Cys Gly Pro Ala His Pro Gly Phe Ser Asp Ser Val Gln
         210                 215                 220

Val Asp Arg Tyr Trp His Thr Met His Gly Asn Trp Thr Leu Gln Tyr
225                 230                 235                 240

Gly Phe Ala Lys Pro Ser Glu Gln Ser Phe Lys Phe Glu Glu Gly Thr
                245                 250                 255

Asp Ala Ala Phe His Gly Phe Trp Leu Trp Pro Cys Thr Met Leu Asn
                260                 265                 270

Val Thr Pro Ile Lys Gly Met Met Thr Val Ile Tyr Glu Phe Pro Val
            275                 280                 285

Asp Ser Glu Thr Thr Leu Gln Asn Tyr Asp Ile Tyr Phe Thr Asn Glu
            290                 295                 300

Glu Leu Thr Asp Glu Gln Lys Ser Leu Ile Glu Trp Tyr Arg Asp Val
305                 310                 315                 320

Phe Arg Pro Glu Asp Leu Arg Leu Val Glu Ser Val Gln Lys Gly Leu
                325                 330                 335

Lys Ser Arg Gly Tyr Arg Gly Gln Gly Arg Ile Met Ala Asp Ser Ser
                340                 345                 350

Gly Ser Gly Ile Ser Glu His Gly Ile Ala His Phe His Asn Leu Leu
            355                 360                 365

Ala Gln Val Phe Lys Asp
    370

<210> SEQ ID NO 5
<211> LENGTH: 966
<212> TYPE: DNA
<213> ORGANISM: Escherichia coli str. K-12 substr. DH10B

<400> SEQUENCE: 5
atgtcagact atcaaatgtt tgaagtacag gtgagccagg ttgaacccct taccgaacag      60
gtgaaacgct tcacgctggt ggcaaccgat ggcaaaccat acctgcgtt accggagga      120 agtcacgtca ttgtgcagat gagcgatggt gataaccagt acagcaatgc gtattcacta     180
ctgagttcgc cgcatgacac ctcttgttat cagattgccg ttcggctgga ggaaaactcg     240
cgcggcggtt cccgcttttt gcatcagcag gtaaaagtgg gcgatcggtt aacgatttca     300
acgcctaata acctgtttgc gctaattccc tcagccagaa agcatctgtt tatcgcgggc     360
ggtattggta tcaccccttt cctgtcgcac atggcagagc tgcaacacag cgacgtcgac     420
tggcagctac attactgctc gcgaaatcca gaaagttgcg catttcgtga tgagctagtc     480
cagcatccgc aggctgagaa agtccatttg catcattcat caaccggaac acgactggaa     540
ttagcgcgat tattggcgga tatcgaacct ggcacacacg tttatacctg tggccccgag     600
gcgctaattg aagcggtaag aagtgaagct gcgcgtctgg acatcgccgc cgatacgctg     660
cactttgagc aatttgctat cgaagacaaa accggcgatg catttaccct ggtgcttgcc     720
cgttccggaa aagagtttgt ggtgccggaa gagatgacta ttttgcaggt tattgaaaat     780
aataaagccg cgaaagtgga atgtttatgt cgtgaagggg tatgcggaac ctgcgaaaca     840
gcaatactgg aaggtgaagc tgaccatcgg gatcaatatt ttagcgatga agagcgtgcc     900
agccagcaaa gtatgttgat ctgttgttcg cgtgcgaagg gtaaacgcct ggtgttggat     960
ttgtag                                                                966

<210> SEQ ID NO 6
<211> LENGTH: 321

<212> TYPE: PRT
<213> ORGANISM: Escherichia coli str. K-12 substr. DH10B

<400> SEQUENCE: 6

Met Ser Asp Tyr Gln Met Phe Glu Val Gln Val Ser Gln Val Glu Pro
1               5                   10                  15

Leu Thr Glu Gln Val Lys Arg Phe Thr Leu Val Ala Thr Asp Gly Lys
            20                  25                  30

Pro Leu Pro Ala Phe Thr Gly Gly Ser His Val Ile Val Gln Met Ser
        35                  40                  45

Asp Gly Asp Asn Gln Tyr Ser Asn Ala Tyr Ser Leu Leu Ser Ser Pro
    50                  55                  60

His Asp Thr Ser Cys Tyr Gln Ile Ala Val Arg Leu Glu Glu Asn Ser
65                  70                  75                  80

Arg Gly Gly Ser Arg Phe Leu His Gln Gln Val Lys Val Gly Asp Arg
                85                  90                  95

Leu Thr Ile Ser Thr Pro Asn Asn Leu Phe Ala Leu Ile Pro Ser Ala
            100                 105                 110

Arg Lys His Leu Phe Ile Ala Gly Gly Ile Gly Ile Thr Pro Phe Leu
        115                 120                 125

Ser His Met Ala Glu Leu Gln His Ser Asp Val Asp Trp Gln Leu His
    130                 135                 140

Tyr Cys Ser Arg Asn Pro Glu Ser Cys Ala Phe Arg Asp Glu Leu Val
145                 150                 155                 160

Gln His Pro Gln Ala Glu Lys Val His Leu His His Ser Ser Thr Gly
                165                 170                 175

Thr Arg Leu Glu Leu Ala Arg Leu Leu Ala Asp Ile Glu Pro Gly Thr
            180                 185                 190

His Val Tyr Thr Cys Gly Pro Glu Ala Leu Ile Glu Ala Val Arg Ser
        195                 200                 205

Glu Ala Ala Arg Leu Asp Ile Ala Ala Asp Thr Leu His Phe Glu Gln
    210                 215                 220

Phe Ala Ile Glu Asp Lys Thr Gly Asp Ala Phe Thr Leu Val Leu Ala
225                 230                 235                 240

Arg Ser Gly Lys Glu Phe Val Val Pro Glu Glu Met Thr Ile Leu Gln
                245                 250                 255

Val Ile Glu Asn Asn Lys Ala Ala Lys Val Glu Cys Leu Cys Arg Glu
            260                 265                 270

Gly Val Cys Gly Thr Cys Glu Thr Ala Ile Leu Glu Gly Glu Ala Asp
        275                 280                 285

His Arg Asp Gln Tyr Phe Ser Asp Glu Glu Arg Ala Ser Gln Gln Ser
    290                 295                 300

Met Leu Ile Cys Cys Ser Arg Ala Lys Gly Lys Arg Leu Val Leu Asp
305                 310                 315                 320

Leu

<210> SEQ ID NO 7
<211> LENGTH: 50
<212> TYPE: PRT
<213> ORGANISM: Artificial sequence
<220> FEATURE:
<223> OTHER INFORMATION: Synthetic

<400> SEQUENCE: 7

Thr Thr Leu Ser Lys Ser Leu Ala Gly Ala Ala Lys His Glu Arg Lys
1               5                   10                  15

```
Ala Ala Lys Thr Leu Gly Ile Ala Val Gly Ile Tyr Leu Leu Cys Trp
         20                  25                  30

Leu Pro Phe Thr Ile Asp Thr Met Val Asp Ser Leu Leu His Phe Ile
        35                  40                  45

Thr Pro
    50
```

TREATING DISEASE AND PROMOTING WEIGHT LOSS BY INHIBITING THE TMA/FMO3/TMAO PATHWAY

The present application claims priority to U.S. Provisional application Ser. No. 62/521,872, filed Jun. 19, 2017, which is herein incorporated by reference in its entirety.

This invention was made with government support under HL103866, awarded by the National Institutes of Health. The government has certain rights in the invention.

SEQUENCE LISTING

The text of the computer readable sequence listing filed herewith, titled "2018-06-19_35298WO1ORD_SQL_ST25", created Jun. 19, 2018, having a file size of 10,556 bytes, is hereby incorporated by reference in its entirety.

FIELD OF THE INVENTION

Provided herein are compositions, systems, and methods for causing weight loss and treating and/or preventing a disease or condition, such as obesity, diabetes, and cancer, with an agent or procedure that inhibits the TMA/FMO3/TMAO pathway in a subject.

BACKGROUND

The incidence of obesity has increased dramatically throughout the world. By the year 2000, a total of 38.8 million American adults or 30% of the population of that country were classified as obese. Obesity is associated with or thought to cause a number of diseases or disorders, and estimates attribute approximately 280,000 deaths each year in the United States to obesity related disorders.

Obesity is a risk factor for developing many obesity-related complications, from non-fatal debilitating conditions, such as, for example, osteoarthritis and respiratory disorders, to life-threatening chronic disorders, such as, for example, hypertension, type 2 diabetes, atherosclerosis, cardiovascular disease, some forms of cancer and stroke. As the number of subjects that are obese is increasing, the need to develop new and effective strategies in controlling obesity and obesity-related complications is becoming increasingly important.

Despite the high prevalence of obesity and many advances in our understanding of how it develops, current therapeutic strategies have persistently failed to achieve long-term success. Moreover, of the subjects that do lose weight, approximately 90 to 95 percent of subsequently regain their lost weight.

SUMMARY OF THE INVENTION

Provided herein are compositions, systems, and methods for causing weight loss and treating and/or preventing a disease or condition, such as obesity, diabetes, and cancer, with an agent or procedure that inhibits the TMA/FMO3/TMAO pathway in a subject.

In some embodiments, provided herein are methods of treating or preventing a disease or condition or causing weight loss comprising: treating a subject with: a) a first agent or first procedure that inhibits the TMA/FMO3/TMAO pathway to cause weight loss, and/or treat or prevent a first disease or first condition, or b) a second agent or second procedure that is a non-antibiotic that inhibits the TMA/FMO3/TMAO pathway to treat or prevent a second disease or second condition, wherein the first disease or first condition is selected from the group consisting of: obesity, dyslipidemia, arthritis pain, sleep apnea, diabetes-associated neuropathy, diabetes-associated cardiovascular disease, diabetes-associated cerebrovascular disease, diabetes-associated peripheral vascular disease, diabetes-associated retinopathy, diabetes-associated nephropathy, diabetes-associated ulceration, colorectal cancer, hepatocellular carcinoma, clear cell renal carcinoma, alcoholic steatohepatitis (ASH), alcoholic cirrhosis, HCV-driven liver fibrosis, HBV-driven liver fibrosis, primary sclerosing cholangitis (PSC), biliary atresia, gall stones, cholestasis, Cushing syndrome, impaired glucose tolerance, prediabetes, hyperglycemia, elevated insulin state, weight management, and arterial aneurysms, and wherein the second disease or second condition is selected from the group consisting of: diabetes mellitus, insulin resistance, metabolic syndrome, nonalcoholic fatty liver disease (NAFD), and nonalcoholic steatohepatitis (NASH). In certain embodiments, the subject has, or is suspected of having, the first disease or condition and/or the second disease or condition. In certain embodiments, the subject is over-weight, but not obese. In some embodiments, the subject is not overweight, but is nonetheless wanting to lose weight.

In certain embodiments, the first agent or procedure and/or the second agent or procedure is selected from the group consisting of: i) 3,3-dimethyl-1-butanol (DMB) or a DMB derivative or related compound; ii) acetylsalicylic acid with or without an enteric coating; iii) an acetylsalicylic acid derivative with or without an enteric coating; iv) a flavin monooxygenase 3 (FMO3) inhibitor; v) a gut TMA lyase inhibitor (e.g., iodomethyl choline); vi) fecal microbiota transplantation; vii) delivery of acetylsalicylic acid or derivative thereof directly to the colon or cecum of the subject; viii) a probiotic or prebiotic that reduces TMA production in the gut; ix) an antiplatelet agent; x) a TMA and/or TMAO sequestering agent; xi) a moiety from Table 1; xii) a compound comprising at least one of: N,N-dimethylethanolamine (DMEA), N-methylethanolamine (MEA), ethanolamine (EA), trimethylsilyl ethanol, P-choline, and P,P,P-trimethyl ethanolphosphine; and xiii) an agent that inhibits trimethylamine-induced human trace amine-associated receptor 5 (TAAR5) activation. In particular embodiments, the first agent comprises an antibiotic or antimicrobial that reduces trimethylamine (TMA) production in the gut. In certain embodiments, the agent that inhibits trimethylamine-induced human trace amine-associated receptor 5 (TAAR5) activation is selected from the group consisting of: an anti-TAAR5 monoclonal antibody or antigen binding portion thereof (e.g., DCABH-17026 from CREATIVE DIAGNOSTICS), TIMBEROL (1-(2,2,6-Trimethylcyclohexyl)hexan-3-ol), an inhibitory peptide (e.g., 33R-9324 from FITZGERALD, which has an amino acid sequence: TTLSKSLAGAAKHERKAAKTLGIA-VGIYLLCWLPFTIDTMVDSLLHFITP, SEQ ID NO:7), or a small molecule (e.g., Compound 1 and Compound 2 from Cichero et al., Med. Chem. Commun., 2016, 7, 353-364, which is herein incorporated by reference in its entirety). Compounds 1 and 2 from Cichero et al. are shown below:

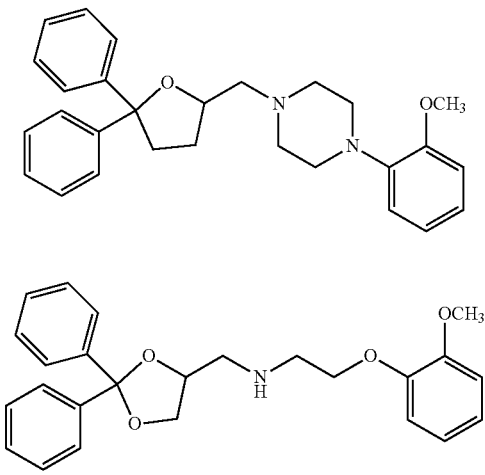

In certain embodiments, a sample from the subject is assayed to determine levels of trimethylamine N-oxide (TMAO), TMA (trimethylamine), FMO3 mRNA, and/or a TMA-containing compound prior to and/or after the treating. In particular embodiments, the subject is identified as having elevated levels of TMA, TMAO, or FMO3 mRNA.

In some embodiments, the DMB derivative or related compound is as shown in Formula I below:

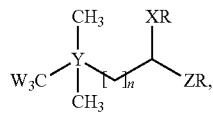

wherein n is an integer, or n is 0, indicating that $CH_2$ is not present;
wherein Y is C, N, Si, P, S, Ge, Sn, Pb, P, As, Sb, or Bi;
wherein each W is independently selected from: H, Cl, F, Br, or I;
wherein X is O, or S, and the corresponding bond is either present or absent or double,
wherein R is absent, H, an alkyl group, alkenyl group, alkynyl group, phenyl group, amide, alkylamide, or a benzyl group;
wherein Z is C, $CH_2$, CH, O, NH, or S,
wherein XR is, alternatively, H, an ester, thioester, or thionester; glycerol, or one of the following three formulas:

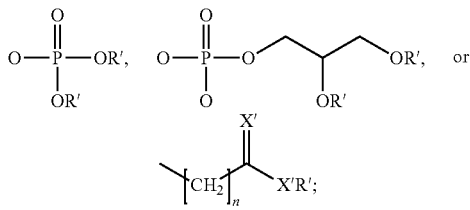

wherein R' is H, an alkyl group, alkenyl group, alkynyl group, phenyl group, or a benzyl group; and wherein X' is O, or S.
In certain embodiments, the acetylsalicylic acid derivative is 5-aminosalysillic acid. In other embodiments, the FMO3 inhibitor comprises Tenofovir, Methimazole, an anti-FMO3 monoclonal or polyclonal antibody or antigen-binding portion thereof, or anti-FMO3 siRNA or shRNA (e.g., anti-FMO3 monoclonal antibody from CREATIVE DIAGNOSTICS, cat. No. DCABH-11586; of anti-FMO3 monoclonal antibody Anti-FMO3 clone OTI1G4 from ORIGENE; or polyclonal FMO3 antibody FMO3 Antibody from SANTA CRUZ BIOTECHNOLOGY, (T-17): sc-51288).

In particular embodiments, the antibiotic is a broad spectrum antibiotic. In other embodiments, the antibiotic is one antibiotic or a combination of antibiotics selected from the group consisting of: metronidazole, ciprofloxacin, and neomycin, amoxicillin. In certain embodiments, the antiplatelet agent is selected from the group consisting of: abciximab, dipyridamole/ASA, anagrelide, cilostazol, clopidogrel, dipyridamole, eptifabatide, prasugrel, ticagrelor, ticlopidine, tirofiban, and vorapaxar. In particular embodiments, the enteric coating provides for release of a majority of the acetylsalicylic acid or the acetylsalicylic acid derivative in the colon or cecum of the subject.

In some embodiments, provided herein are systems system comprising: a) a report for a subject with a first disease, a first condition, a second disease, and/or a second condition, wherein the report indicates that the patient has elevated levels of TMA, FMO3, and/or TMAO; and b) a first agent that inhibits the TMA/FMO3/TMAO pathway to cause weight loss, and/or treat or prevent a first disease or first condition, and/or c) a second agent that is a non-antibiotic that inhibits the TMA/FMO3/TMAO pathway to treat or prevent a second disease or second condition, wherein the first disease or first condition is selected from the group consisting of: obesity, dyslipidemia, arthritis pain, sleep apnea, diabetes-associated neuropathy, diabetes-associated cardiovascular disease, diabetes-associated cerebrovascular disease, diabetes-associated peripheral vascular disease, diabetes-associated retinopathy, diabetes-associated nephropathy, diabetes-associated ulceration, colorectal cancer, hepatocellular carcinoma, clear cell renal carcinoma, alcoholic steatohepatitis (ASH), alcoholic cirrhosis, HCV-driven liver fibrosis, HBV-driven liver fibrosis, primary sclerosing cholangitis (PSC), biliary atresia, gall stones, cholestasis, Cushing syndrome, impaired glucose tolerance, prediabetes, hyperglycemia, elevated insulin state, weight management, and arterial aneurysms, and wherein the second disease or second condition is selected from the group consisting of: diabetes mellitus, insulin resistance, metabolic syndrome, nonalcoholic fatty liver disease (NAFD), and nonalcoholic steatohepatitis (NASH).

In other embodiments, provided here are systems comprising: a) an agent that inhibits the TMA/FMO3/TMAO pathway; and b) equipment that allows delivery of the first agent and/or the second agent directly to the cecum and/or colon of a subject. In certain embodiments, the equipment comprises a suppository and/or an enema system or device.

In certain embodiments, the first agent and/or the second agent is selected from the group consisting of: i) 3,3-dimethyl-1-butanol (DMB) or a DMB derivative or related compound; ii) acetylsalicylic acid with or without an enteric coating; iii) an acetylsalicylic acid derivative with or without an enteric coating; iv) a flavin monooxygenase 3 (FMO3) inhibitor; v) a gut TMA lyase inhibitor (e.g., iodomethyl choline); vi) a probiotic or prebiotic that reduces TMA production in the gut; vii) an antiplatelet agent; viii) a TMA and/or TMAO sequestering agent; ix) a moiety from Table 1; x) a compound comprising at least one of: N,N-dimethylethanolamine (DMEA), N-methylethanolamine (MEA), ethanolamine (EA), trimethylsilyl ethanol, P-choline, and P,P,P-trimethyl ethanolphosphine; and xi) an agent that inhibits trimethylamine-induced human trace amine-associated receptor 5 (TAAR5) activation.

In particular embodiments, the first agent comprises an antibiotic or antimicrobial that reduces trimethylamine (TMA) production in the gut. In other embodiments, the DMB derivative or related compound is as shown in Formula I below:

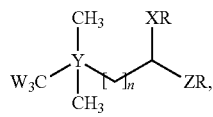

wherein n is an integer, or n is 0, indicating that CH$_2$ is not present;
wherein Y is C, N, Si, P, S, Ge, Sn, Pb, P, As, Sb, or Bi;
wherein each W is independently selected from: H, Cl, F, Br, or I;
wherein X is O, or S, and the corresponding bond is either present or absent or double,
wherein R is absent, H, an alkyl group, alkenyl group, alkynyl group, phenyl group, amide, alkylamide, or a benzyl group;
wherein Z is C, CH$_2$, CH, O, NH, or S,
wherein XR is, alternatively, H, an ester, thioester, or thionester; glycerol, or one of the following three formulas:

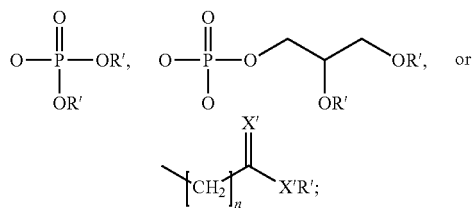

wherein R' is H, an alkyl group, alkenyl group, alkynyl group, phenyl group, or a benzyl group; and wherein X' is O, or S.

In certain embodiments, the acetylsalicylic acid derivative is 5-aminosalysillic acid. In further embodiments, the FMO3 inhibitor comprises Tenofovir, Methimazole, an anti-FMO3 antibody, or anti-FMO3 siRNA or shRNA. In additional embodiments, the antibiotic is a broad spectrum antibiotic. In particular embodiments, the antibiotic is one antibiotic or a combination of antibiotics selected from the group consisting of: metronidazole, ciprofloxacin, and neomycin, amoxicillin. In additional embodiments, the antiplatelet agent is selected from the group consisting of: abciximab, dipyridamole/ASA, anagrelide, cilostazol, clopidogrel, dipyridamole, eptifabatide, prasugrel, ticagrelor, ticlopidine, tirofiban, and vorapaxar. In certain embodiments, the enteric coating provides for release of a majority of the acetylsalicylic acid or the acetylsalicylic acid derivative in the colon or cecum of the subject.

In particular embodiments, rather than, or in addition to treating, the patient is prescribed one of the first or second agents or first or second procedures described herein. In some embodiments, a patient with the first disease or condition or second disease or condition is also, or alternatively, prescribed a diet with reduced levels of carnitine containing compounds (e.g., prescribed a vegetarian or vegan diet). In certain embodiments, the diet is a Mediterranean diet, or diet low in TMAO precursors (e.g., low in choline, lecithin, carnitine, etc.), or low in TMAO (e.g., a diet low in certain fish, such as cod, tilapia, Chilean sea bass, etc.).

In certain embodiments, a sample from the subject is assayed to determine levels of trimethylamine N-oxide (TMAO), TMA, and/or a TMA-containing compound prior to and/or after said treating. In particular embodiments, a subject is found to need treatment if elevated levels of KIM1, TMA, TMAO, FMO3 mRNA, or elevated urine albumin/Creatine ratio are found. In other embodiments, a subject is found to need treatment if decreased levels of eFGF, eCrCl, or increased Cystatin C are found. In other embodiments, the sample comprises whole blood, serum, plasma, exhaled breath, urine, saliva, cerebrospinal fluid, or bronchoalveolar lavage.

In some embodiments, the subject is identified as having elevated levels of TMA, TMAO, and/or FMO3 mRNA. In further embodiments, the identifying comprises viewing results of a TMAO and/or TMA assay (e.g., on paper or on a computer screen) performed on a sample from the subject which show elevated TMAO and/or TMA levels. In certain embodiments, the identifying comprises viewing results of a TMA or TMAO assay performed on a sample or exhaled breath from said subject which show elevated TMA or TMAO levels. In certain embodiments the sample is selected from whole blood, serum, plasma, urine, and saliva.

In other embodiments, the first or second agent is as shown in Formula I below:

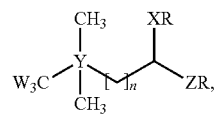

wherein n is an integer, or n is 0, indicating that CH$_2$ is not present;
wherein each W is independently selected from: H, Cl, F, Br, or I (e.g., W$_3$C=CH$_3$, CH$_2$Cl, CH$_2$Fl, CH$_2$Br, CH$_2$I, CF$_3$, CCl$_3$, CBr$_3$, CI$_3$, or CHCl$_2$);
wherein Y is C, N, Si, P, S, Ge, Sn, Pb, P, As, Sb, or Bi;
wherein X is O or S and the corresponding bond is either present or absent or double,
wherein R is absent, H, an alkyl group, alkenyl group, alkynyl group, phenyl group, amide, alkylamide, or a benzyl group;
wherein Z is C, CH$_2$, CH, NH, O, or S,
wherein XR is, alternatively, H, an ester, thioester, or thionester; glycerol, or one of the following three formulas:

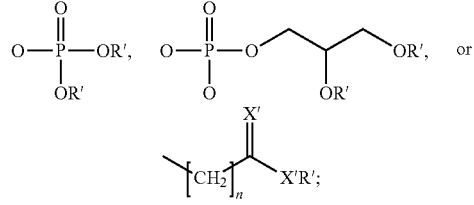

wherein R' is H, an alkyl group, alkenyl group, alkynyl group, phenyl group, or a benzyl group; and wherein X' is O, or S. In certain embodiments, R is amide or alkylamide, and Z is an O, and Z as a double bond O—a carboxylic acid). In some embodiments, the two methyl groups extending from Y are linked by an alkyl or ether to form a 4-6 member ring.

In further embodiments, the acetylsalicylic acid derivative or related compound is selected from the group consisting of: 4-Methylsalicylic acid, 5-(acetylamino)-2-hydroxybenzoic acid; Salicylic acid, sodium salt, 4-Aminosalicylic acid, 3-Methylsalicylic acid, 3-Nitrosalicylic acid, 1-Hydroxy-2-naphthoic acid, 2-Hydroxyethyl salicylate, 5-Bromosalicylic acid, 5-Methylsalicylic acid, 5-Aminosalicylic acid, 2,4-Dihydroxybenzoic acid, 2,4-Dimethoxybenzoic acid, 3-Hydroxy-2-naphthoic acid, 5-Nitrosalicylic acid, Phenyl salicylate, Ethyl salicylate, 5-Iodosalicylic acid, Methyl salicylate, 5,5'-Methylenedisalicylic acid, Pamoic acid, 2-Ethoxybenzoic acid, 2,6-Dihydroxybenzoic acid, 2,3-Dihydroxybenzoic acid, Ochratoxin A, 5-Chlorosalicylic acid, 4-Fluorosalicylic acid, Methyl 5-fluoro-2-hydroxybenzoate, 2,4,5-Trimethoxybenzoic acid, 2,5-Dihydroxybenzoic acid, Acetylsalicylsalicylic acid, Salicylsalicylic acid, 6-Methylsalicylic acid, Aluminon, 3-Aminosalicylic acid, 2,3,4-Trimethoxybenzoic acid, o-Anisic acid, Isopropyl salicylate, 3,5-Dinitrosalicylic acid, 2,3,4-Trihydroxybenzoic acid, 5-Formylsalicylic acid, 2-Hydroxy-4-nitrobenzoic acid, Lithium 3,5-diiodosalicylate, 4-Fluorosulfonyl-1-hydroxy-2-naphthoic acid, 3-Methoxysalicylic acid, Methyl 1-hydroxy-2-naphthoate, Carminic acid, Carmine (pure, alum lake of carminic acid), Carmine (high purity biol.stain, alum lake of carminic acid), 2,6-Dimethoxybenzoic acid, 2,3-Dimethoxybenzoic acid, Chrome Azurol S, Alizarin Yellow R sodium salt, 3-Chlorosalicylic acid, 2-(trifluoromethoxy) benzoic acid, Methyl 2,4-dimethoxybenzoate, Methyl 2,6-dihydroxybenzoate, Methyl 2,4-dihydroxybenzoate, Triethanolamine salicylate, 2-Ethoxynaphthoic acid, 4-Methoxysalicylic acid, 5-Methoxysalicylic acid, 2,5-Dimethoxybenzoic acid, 3,5 Dibromosalicylic acid, 6-Methoxysalicylic acid, 5-Chloro-o-anisic acid, Chromoxane Cyanine R, 3-Hydroxy-4-(2-hydroxy-4-sulfo-1-naphthylazo) naphthalene-2-carboxylic acid, indicator grade ethyl 2,3-dihydroxybenzoate, Methyl 5-iodosalicylate, methyl 5-chloro-2-hydroxybenzoate, Methyl 4-acetamido-5-chloro-2-methoxybenzoate, 2-(acetyloxy)-3-methylbenzoic acid, 2-(acetyloxy)-3-methylbenzoic acid, 1,4-Benzodioxan-5-carboxylic acid, 2-Methoxy-5-(trifluoromethyl)benzoic acid, 4-Chlorosalicylic acid, Methyl 4-methoxysalicylate, 1,3-benzodioxole-4-carboxylic acid, 5-Sulfosalicylic acid dihydrate, 5-Sulfosalicylic acid dihydrate, 5-Sulfosalicylic acid dihydrate, Mordant Yellow 10, 4-Amino-5-chloro-2-methoxybenzoic acid, Methyl 5-acetylsalicylate, 5-chlorosulfonyl-2-hydroxybenzoic acid, methyl 2-[2-(dimethylamino)ethoxy]benzoate, alpha-Apo-oxytetracycline, beta-Apo-oxytetracycline, 3,5-Di-tert-butylsalicylic acid, Methyl 3,5-dibromo-2-hydroxybenzoate, 2-(3-methoxyphenoxy) benzoic acid, Methyl 3-nitrosalicylate, Methyl 5-methylsalicylate, methyl 4-amino-2-methoxybenzoate, chroman-8-carboxylic acid, methyl 2,5-di(2,2,2-trifluoroethoxy) benzoate, 2,3 dihydrobenzo[b]furan-7-carboxylic acid, methyl 3-amino-2-hydroxybenzoate, 3-chloro-2,6-dimethoxybenzoic acid, 3-Hydroxyphthalic anhydride, 5-Bromo-2,3-dihydrobenzo[b]furan-7-carboxylic Acid, 2,2-dimethyl-2,3-dihydro-1-benzofuran-7-carboxylic acid, 6-Fluorosalicylic acid, 2,4,6-Trihydroxybenzoic acid monohydrate, 3-bromo-2,6-dimethoxybenzoic acid, 3-bromo-2,6-dimethoxybenzoic acid, 3,5-dichloro-2,6-dimethoxybenzoic acid, Lavendustin A, 2-Fluoro-6-methoxybenzoic acid, 5-Bromo-2,4-dihydroxybenzoic acid monohydrate, 3-chloro-2,6-dimethoxy-5-nitrobenzoic acid, methyl 4,7-dibromo-3-methoxy-2-naphthoate, 2-(trifluoromethoxy)terephthalic acid, 2-methoxy-4,6-di(trifluoromethyl)benzoic acid, 2-[2-(dimethylamino)ethoxy]benzoic acid, 2-[(5-chloro-3-pyridyl)oxy]-5-nitrobenzoic acid, 6-fluoro-4H-1,3-benzodioxine-8-carboxylic acid, 3-Methoxy-4-(methoxycarbonyl)phenylboronic acid pinacol ester, 3-Methoxy-4-(methoxycarbonyl)phenylboronic acid, 2-(tetrahydropyran-4-yloxy)benzoic acid, pentafluorophenyl 2-(tetrahydro-2H-pyran-4-yloxy)benzoate, 3-Hydroxy-4-(methoxycarbonyl) phenylboronic acid pinacol ester, and 3-Formylsalicylic acid hydrate.

In some embodiments, the TMA and/or TMAO sequestering agent comprises activated charcoal or copper chlorophyllin (e.g., activated charcoal at 750 mg 2×/day for 10 days, or copper chlorophyllin at 60 mg 3×/day after meals for 3 weeks).

BRIEF DESCRIPTION OF THE FIGURES

FIG. 1A shows the relationship of fasting plasma TMAO concentrations and prevalent T2DM. Boxes represent the 25th, 50th and 75th percentiles of plasma TMAO concentration, and whiskers represent the 10th and 90th percentiles. FIG. 1B shows the relationship of fasting plasma choline concentrations and prevalent T2DM. Boxes represent the 25th, 50th and 75th percentiles of plasma choline concentration, and whiskers represent the 10th and 90th percentiles. FIG. 1C shows forest plots of the odds ratio of prevalent T2DM and quartiles of TMAO; bars represent 95% confidence intervals. FIG. 1D shows forest plots of the odds ratio of prevalent T2DM and quartile of choline; bars represent 95% confidence intervals.

FIG. 2. Plasma TMAO levels in mice and FMO3 mRNA expression in men demonstrate positive correlations with obesity. Panels A-D show the correlation of plasma trimethylamine-N-oxide (TMAO) levels with obesity-related traits in 180 male mice from 92 inbred strains within the hybrid mouse diversity panel (HMDP) after 8 week feeding of a high fat and high sucrose diet. Correlation coefficient (r) and p value (p) are indicated for each obesity trait. FIG. 2A shows the correlation between plasma TMAO and body weight. FIG. 2B shows the correlation between plasma TMAO and fat mass. FIG. 2C shows the correlation between plasma TMAO and mesenteric fat weight. FIG. 2D shows the correlation between plasma TMAO and subcutaneous fat weight. FIG. 2E shows the correlations between human white adipose tissue flavin monooxygenase 3 (FMO3) mRNA expression and metabolic traits or brown/beige adipocyte marker gene expression (n=770). The gene name and probeset ID is provided for each of the brown/beige adipocyte marker genes.

FIG. 3A, top panel, shows: CRISPR-Cas9 strategy for generating Fmo3−/− mice. The sequence of exon 2 of the murine Fmo3 coding sequence is shown (SEQ ID NO:1). The target sequence (underlined; SEQ ID NO:2) used for construction of the guide RNA is shown with arrows indicating predicted cleavage sites by Cas9. Bottom panel: immunoblotting analysis of FMO3 protein levels in the livers of wild-type (WT) and Fmo3−/− (KO) mice. FIG. 3B shows decreased adiposity in Fmo3−/− mice. Fmo3+/+(n=9), Fmo3+/−(n=6), and Fmo3−/− (n=11) mice were fed a 1.3% choline chloride (w/w) diet for 12 weeks before tissue collection. Plasma TMAO and TMA levels (top left), food intake (top right), body weight (bottom left) and 4 fat pads/body weight (%; bottom right) are shown. The four fat pads included in the 4 fat pads/body weight measurement were gonadal, mesentery, perirenal, and subcutaneous. *: p≤0.05 between Fmo3+/+ and Fmo3−/− groups. &: p≤0.05 between Fmo3+/− and Fmo3−/− genotype groups.

Figure 1:
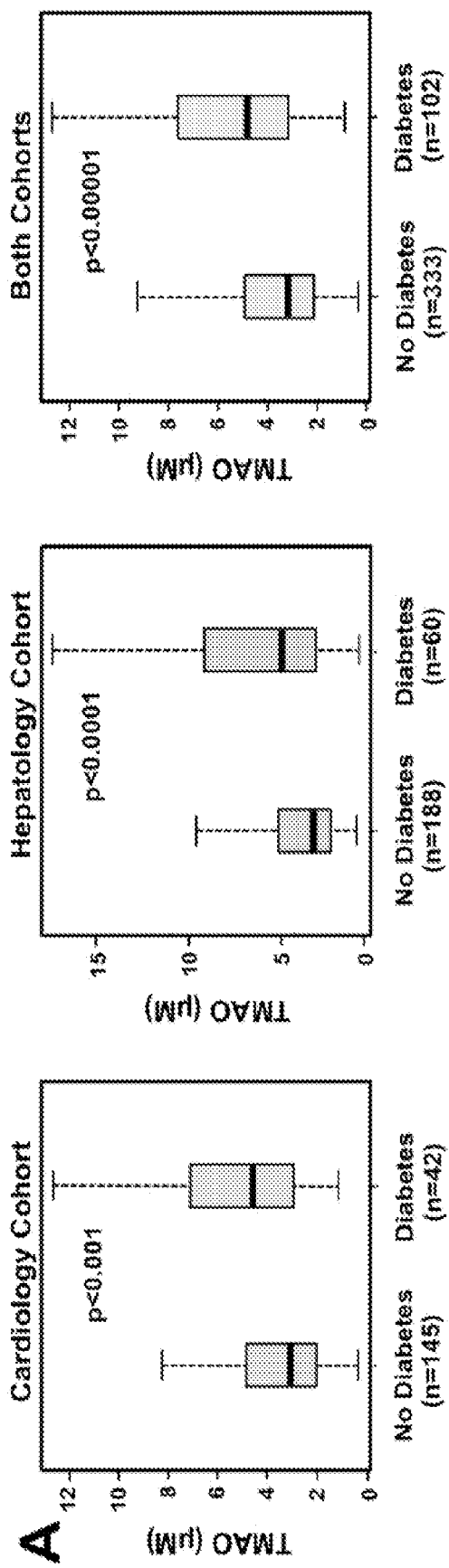
FIG. 1. Elevated Circulating Levels of TMAO are associated with Type 2 diabetes Mellitus in humans. Two separate cohorts of stable subjects in preventative cardiology (n=187) or hepatology clinics (n=248) were recruited to evaluate associations between fasting circulating choline or trimethylamine-N-oxide (TMAO) levels with prevalent type 2 diabetes (T2DM). The total number of subjects recruited in both studies was n=435.
Figure 1:
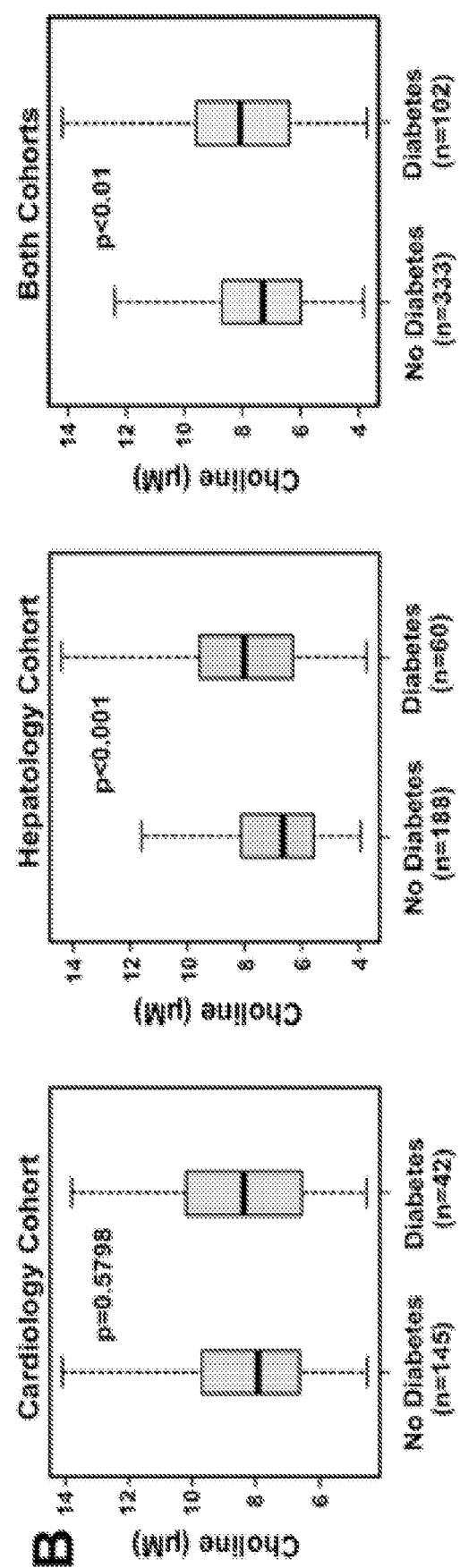
Figure 1:
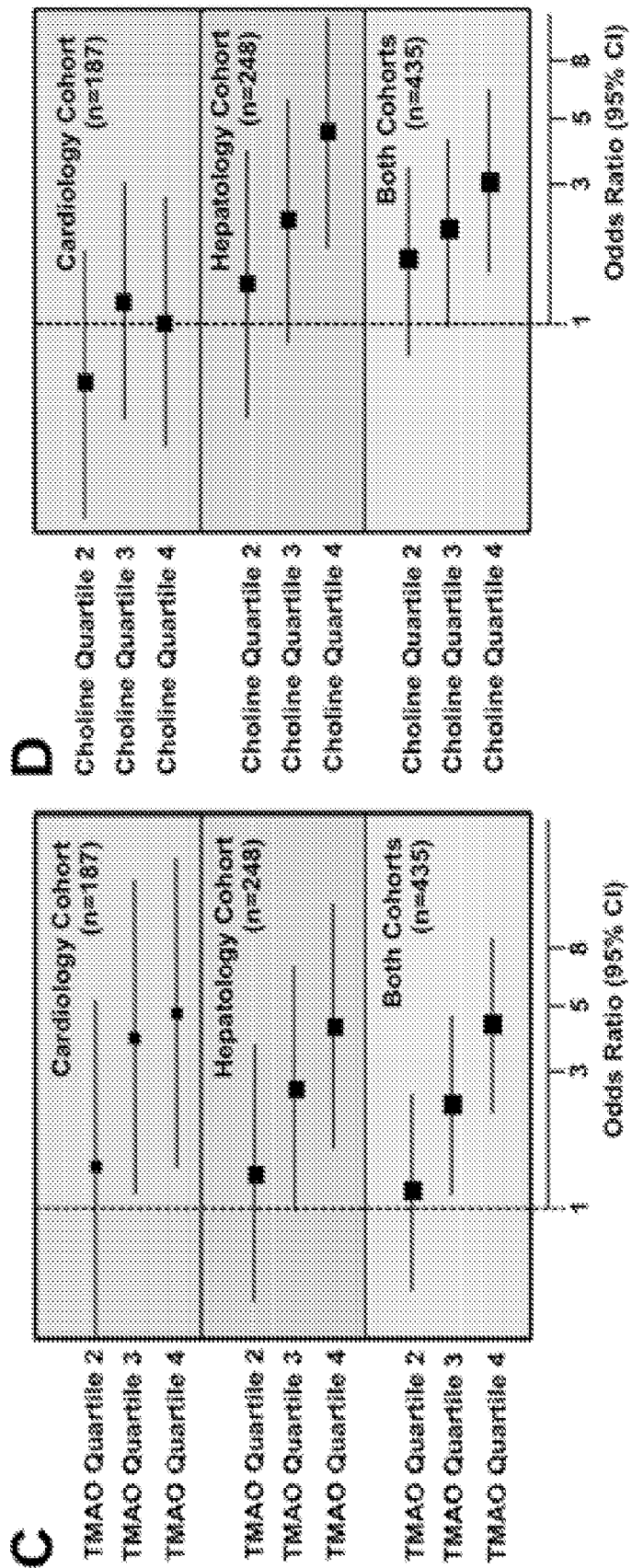

Panels (C-H) Ldlr−/−; Fmo3−/− mice are more resistant to obesity than Ldlr−/− littermates when fed a Western diet for 12 weeks. FIG. 3C shows liver FMO activity, while FIG. 3D shows plasma TMAO levels. FIG. 3E shows body weight changes over 12 weeks, while FIG. 3F shows fat mass/body weight (%). FIG. 3G shows four fat pad weight/body weight (%); the 4 fat pads measured were gonadal, mesentery, perirenal, and subcutaneous. FIG. 3H shows gene expression analysis of subcutaneous fat pads of Ldlr−/− (n=17) and Ldlr−/−; Fmo3−/− (n=9) mice. Cell death-inducing DFFA-like effector A (Cidea), Cytochrome C oxidase subunit 8b (Cox8b), Elongation of very long chain fatty acids protein 3 (Elovl3), Uncoupling protein 1 (Ucp1), Diglyceride acyl-transferase 1 (Dgat1), Leptin (Lep), Stearoyl CoA desaturase-1 (Scd1), Transducin-like enhancer of split 3 (Tle3)*, p≤0.05, , p≤0.01, and *, p≤0.0001 between the two genotype groups.

FIG. 4 shows the nucleic acid sequence (SEQ ID NO:3) and amino acid sequence (SEQ ID NO:4) of the *E. Coli* yeaW gene and protein.

FIG. 5 shows the nucleic acid sequence (SEQ ID NO:5) and amino acid sequence (SEQ ID NO:6) of the *E. Coli* yeaX gene and protein.

Figure 6:
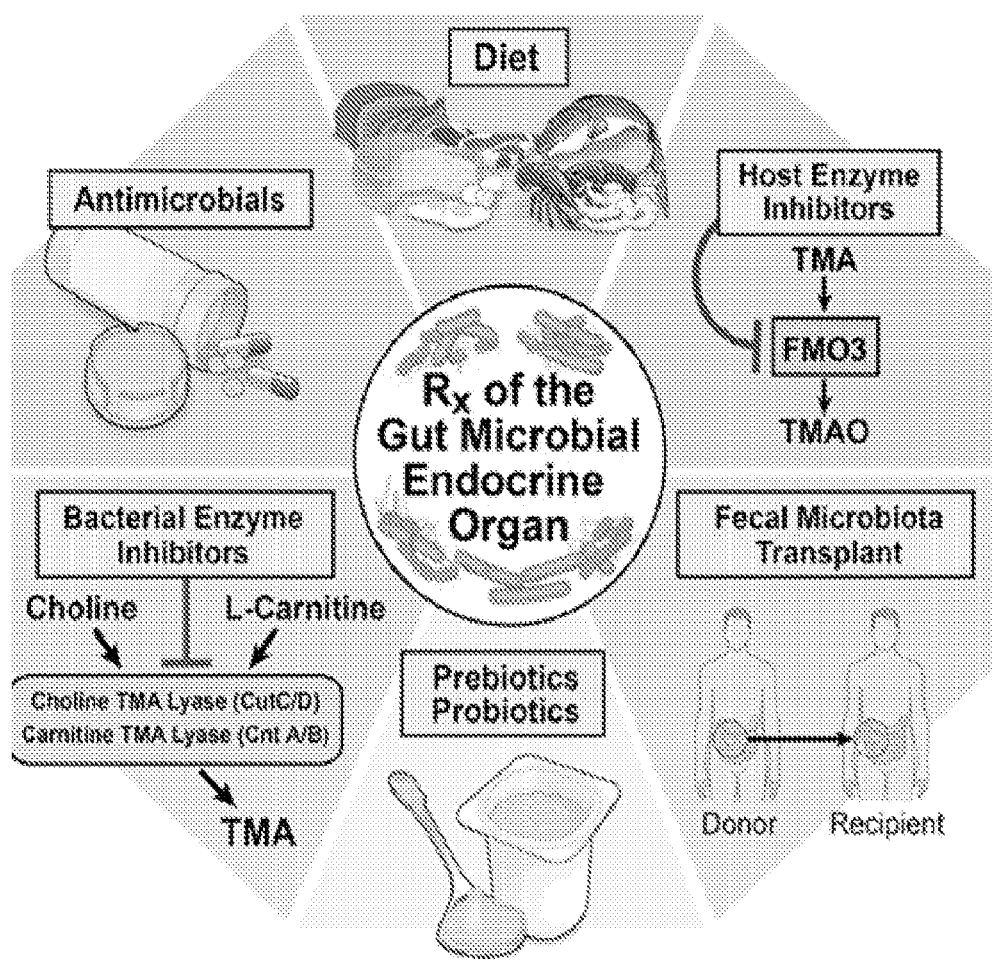

FIG. 6 provides a schematic with exemplary strategies to target the gut microbial endocrine organ (e.g., for treating obesity, diabetes, cancer, and to induce weight loss). Strategies for manipulating gut microbiota include, for example: 1) Dietary manipulation, 2) Prebiotics or Probiotics, 3) Fecal Microbiota Transplantation, 4) Antimicrobials/antibiotics, 5) Bacterial Enzyme Inhibitors (e.g., TMA lyase inhibitors), or 6) Host Enzyme Inhibitors (e.g., flavin monooxygenase 3 (FMO3) inhibitors).

Figure 7:
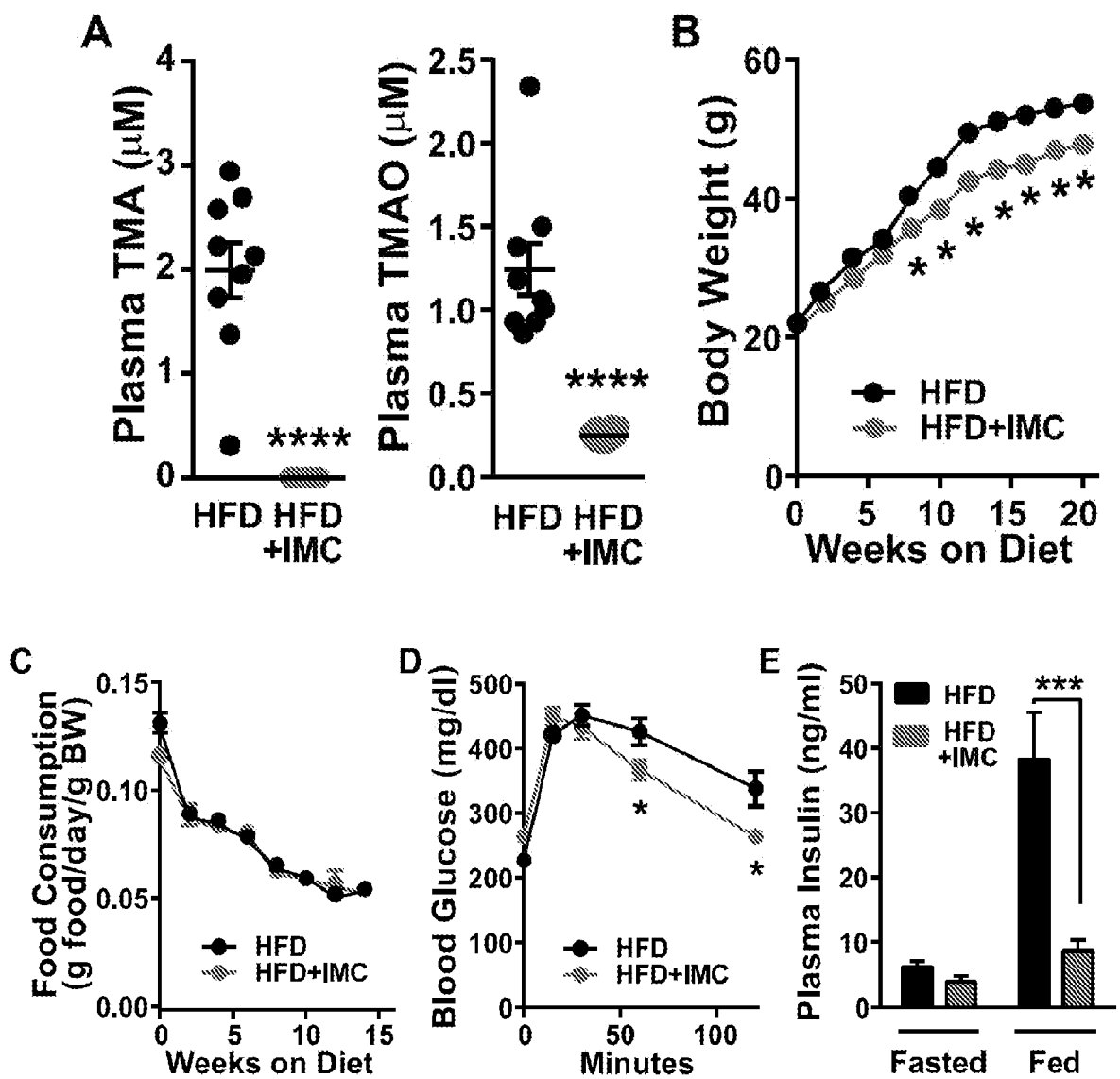
Figure 7:
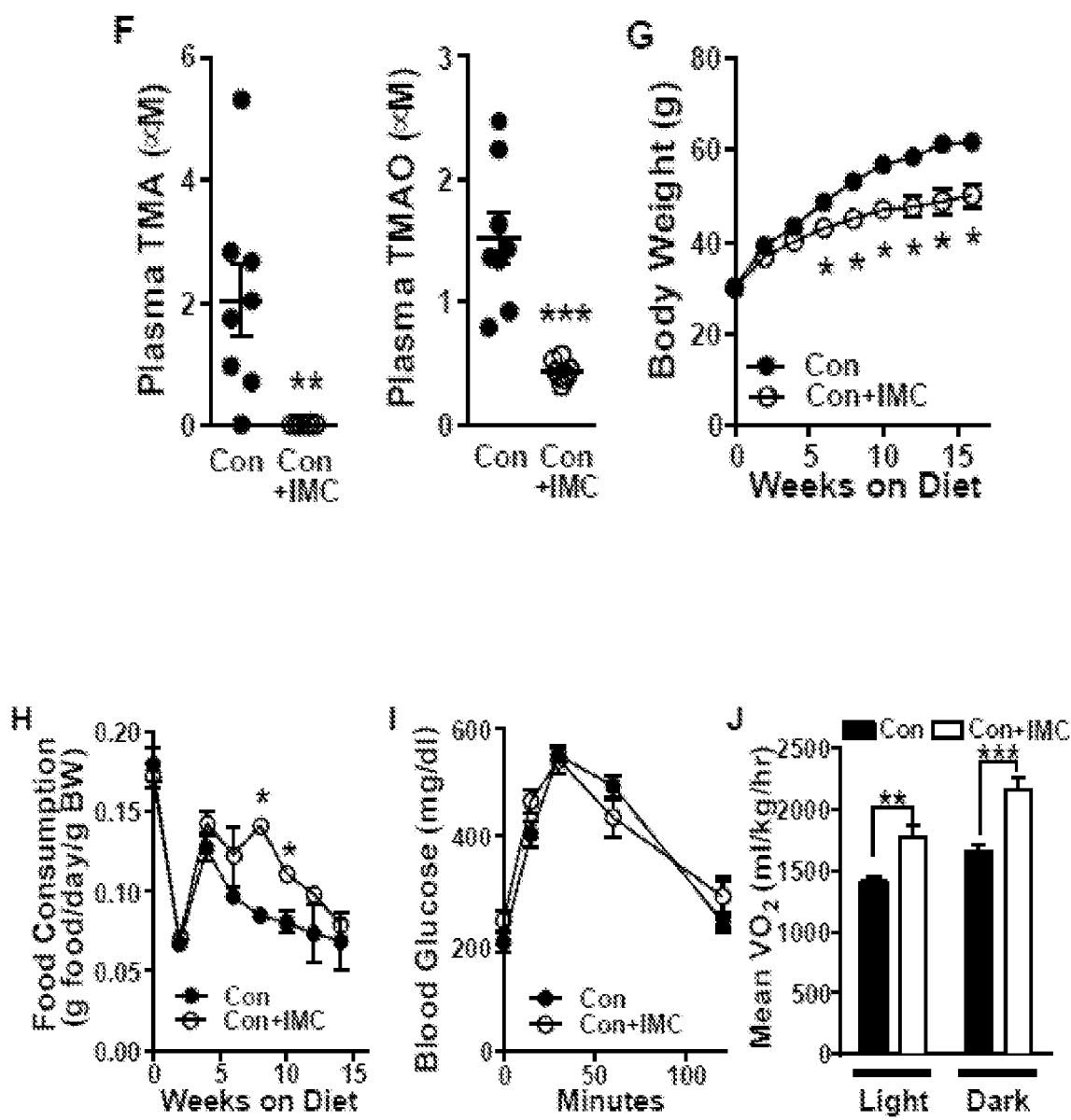
Figure 7:
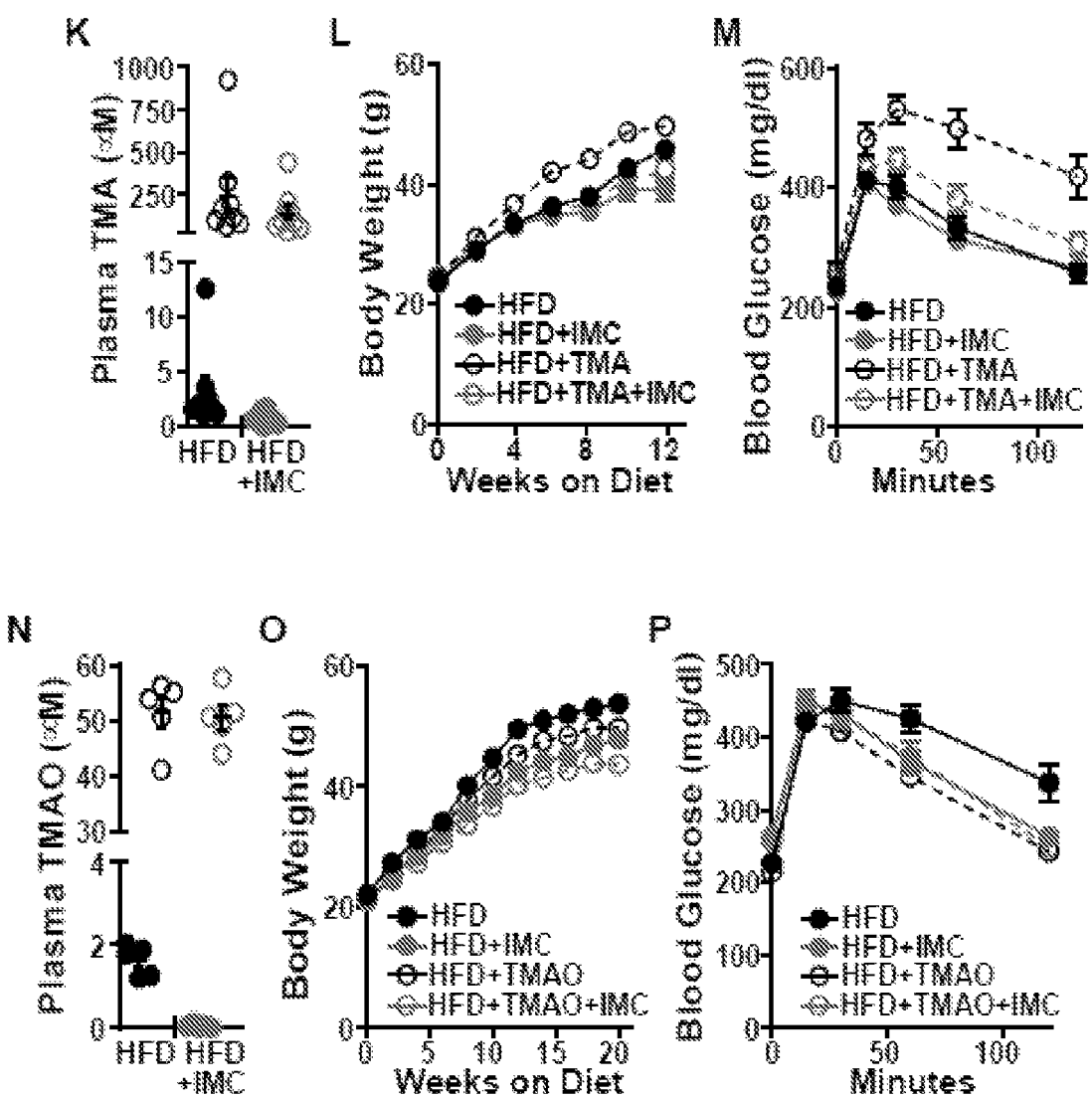

FIG. 7(A-E) shows the results of Example 2 where mice were fed a high fat diet with or without a TMA lyase inhibitor for 20 weeks: A) Plasma TMA and TMAO levels (uM); B) Body weight (g); C) Food consumption normalized to body weight (g of diet consumed per day per g of body weight); D) Glucose tolerance measured after 12 weeks on diet; and E) Plasma insulin measured following an overnight fast (Fasted) or 4 hours postprandially (Fed); n=4-5 mice/group. *, p<0.05, *, p<0.001, **, p<0.0001 vs HFD-fed mice.

FIG. 7(F-J) shows the results of Example 2 where mice were fed a control diet with or without a TMA lyase inhibitor for 16 weeks: F) Plasma TMA and TMAO levels (uM); G) Body weight (g); H) Food consumption normalized to body weight (g of diet consumed per day per g of body weight); I) Glucose tolerance measured after 12 weeks on diet; and J) Mean oxygen consumption (VO2; ml/kg/hr) measured after 5 weeks on diet; n=6 mice/group. *, p<0.05, , p<0.01, *, p<0.001 vs Control-fed mice.

FIG. 7 (K-P) shows the results of Example 2 where mice were fed a high fat diet (HFD) or HFD+IMC, which was supplemented with either 100 mM TMA in the drinking water (K-M) or 0.3% w/w TMAO in the diet (N-P). HFD and HFD+IMC data in panels 7 N-P are the same as those depicted in 7 A, B, and D above, and have been replicated here for comparison. Figure K-P show: K) Plasma TMA and TMAO levels (uM) after 6 weeks on diet and TMA supplementation; L) Body weight (g) over 12 weeks; M) Glucose tolerance measured after 10 weeks on diet and TMA supplementation; N) Plasma TMA and TMAO levels (uM) after 12 weeks on diet and TMAO supplementation; O) Body weight (g) over 20 weeks; and P) Glucose tolerance measured after 12 weeks on diet and TMAO supplementation.

Figure 8:
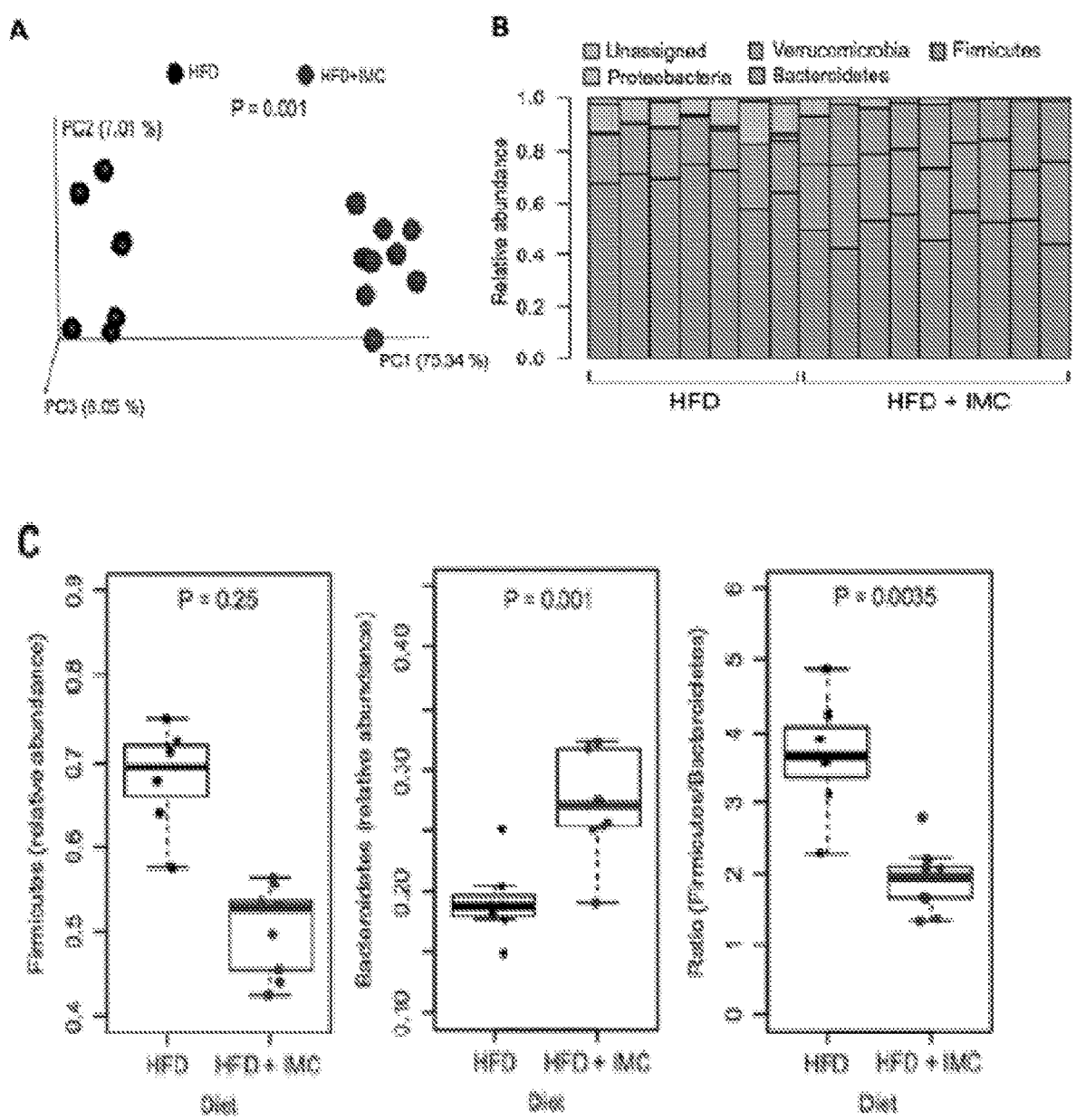
Figure 8:
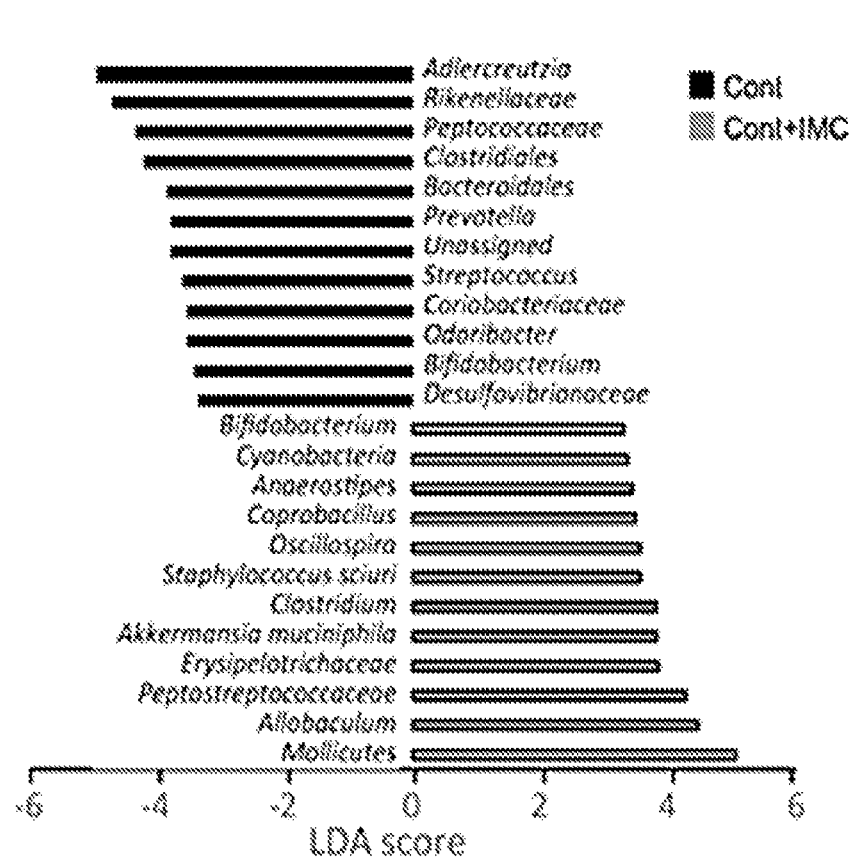
Figure 8:
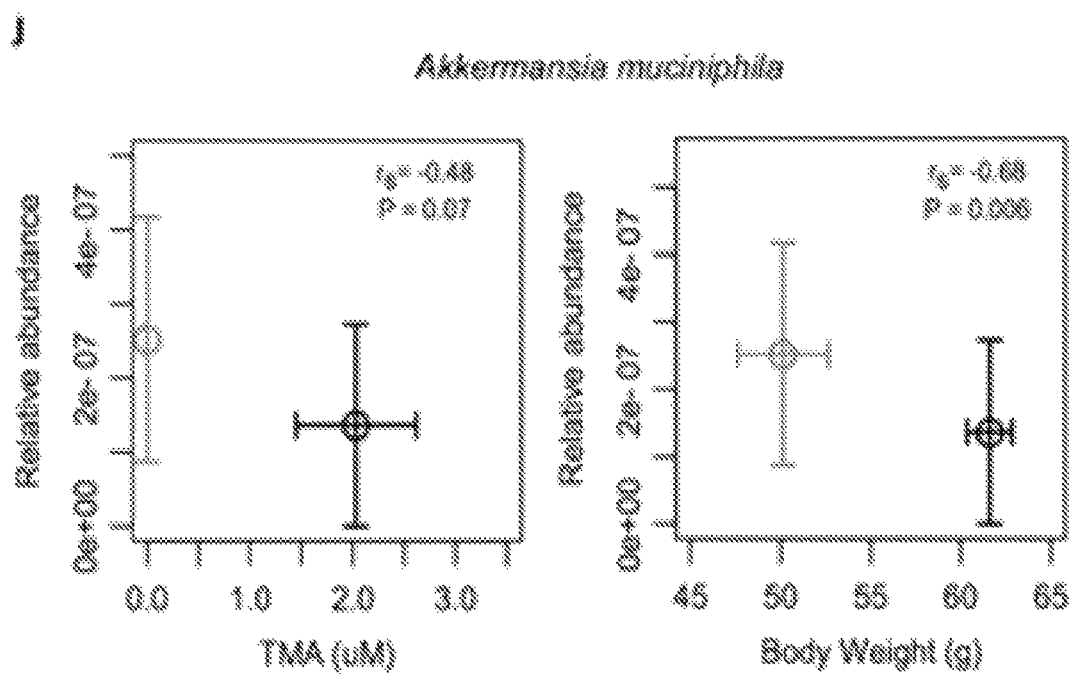
Figure 8:
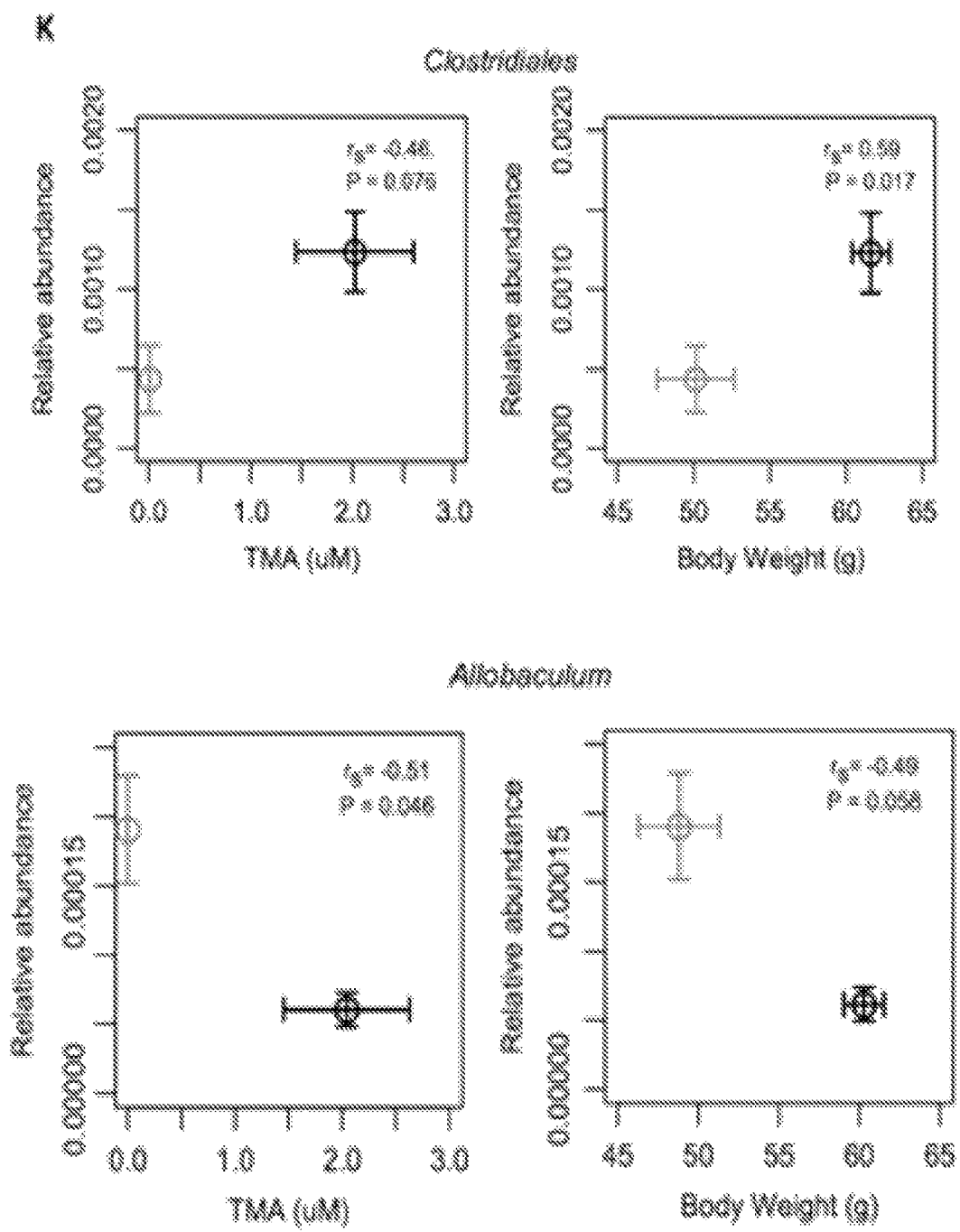

FIG. 8 shows that lyase inhibitor IMC alters the cecum microbiota composition in models of high fat diet-induced and leptin deficient obesity. FIG. 8A-F represents data from HFD model and G-K the Ob/Ob model. Fig. A,G. Principal co-ordinate analysis (PCoA) plot of microbiota profiles built from weighted Unifrac distances. Each point represents a single sample from a single mouse. Positions of points in space display dissimilarities in the microbiota, with points further from one another being more dissimilar. FIG. 8B,H. Barplot of cecal microbiota at the phylum level. Each bar represents an individual mouse and each color an individual phyla. FIG. 8C. Relative abundance of Firmicutes, Bacteroidetes and the Firmicutes to Baceteroidetes ratio for mice on HFD with or without IMC. The boxes represent the 25th and 75th quartiles, and the line displays the median value within each group.

FIG. 8 also shows that lyase inhibitor IMC alters the cecum microbiota composition in models of high fat diet-induced and leptin deficient obesity. FIG. 8A-F represents data from HFD model and G-K the Ob/Ob model. FIG. 8A,G. Principal co-ordinate analysis (PCoA) plot of microbiota profiles built from weighted Unifrac distances. Each point represents a single sample from a single mouse. Positions of points in space display dissimilarities in the microbiota, with points further from one another being more dissimilar. FIG. 8B,H. Barplot of cecal microbiota at the phylum level.

DEFINITIONS

The terms "individual," "host," "subject," and "patient" are used interchangeably herein, and generally refer to a mammal, including, but not limited to, primates, including simians and humans, equines (e.g., horses), canines (e.g., dogs), felines, various domesticated livestock (e.g., ungulates, such as swine, pigs, goats, sheep, and the like), as well as domesticated pets and animals maintained in zoos. In some embodiments, the subject is specifically a human subject.

DETAILED DESCRIPTION OF THE INVENTION

Provided herein are compositions, systems, and methods for causing weight loss and treating and/or preventing a disease or condition, such as obesity, diabetes, and cancer, with an agent or procedure that inhibits the TMA/FMO3/TMAO pathway in a subject.

I. TMA/FMO3/TMAO Pathway

There is strong evidence that microbes resident in the human intestine represent a key environmental factor contributing to obesity and associated insulin resistance (Bäckhed et al., 2004; Ley et al., 2005; Turnbaugh and Gordon, 2009; Cox et al., 2014). However, molecular mechanisms by which gut microbiota promote obesity and insulin resistance in humans are incompletely understood. Recently, several independent groups have identified the gut microbiota-initiated TMA/FMO3/TMAO pathway as a potential modulator of cardiometabolic phenotypes in the host (Wang et al., 2011; Warner et al., 2015; Miao et al., 2015; Shih et al., 2015), although our mechanistic understanding of this meta-organismal pathway is still incomplete.

The TMA/FMO3/TMAO pathway is a microbe-to-host endocrine axis by which gut microbial metabolism of nutrients common in Western diets (phosphatidylcholine, choline, and L-carnitine) results in the production of the metabolite trimethylamine (TMA), which is exclusively generated by certain communities of gut microbiota (Wang et al., 2011; Koeth et al., 2013; Gregory et al., 2015; Romano et al., 2015). Then, the host hepatic enzyme flavin-containing monooxygenase 3 (FMO3) further metabolizes gut microbe-derived TMA to produce trimethylamine-N-oxide (TMAO) (Wang et al., 2011; Bennett et al., 2013). Importantly, the end product of this meta-organismal nutrient metabolism pathway, TMAO, is both a prognostic biomarker and is mechanistically linked to cardiovascular disease (CVD) pathogenesis in humans (Wang et al., 2011; Koeth et al., 2013; Tang et al., 2013; Wang et al., 2014; Koeth et al., 2014; Tang et al., 2014; Suzuki et al., 2016; Missailidis et al., 2016; Mafune et al., 2016; Trøseid et al., 2015; Wang et al., 2015; Zhu et al., 2016). Work conducted during development of embodiments herein identified, among other things, a previously unknown link between the gut microbe-driven TMA/FMO3/TMAO pathway and adipose tissue function. Inhibiting this pathway, which procedures and chemical agents, may be employed to treat various diseases and conditions related to the TMA/FMO3/TMAO pathway.

II. DMB, Derivatives, and Related Compounds

In some embodiments, the agent used to inhibit the TMA/FMO3/TMAO pathway (e.g., to inhibit TMAO production in the gut) is DMB, a DMB derivative, or related compound. In some embodiments, the agent is 3,3-dimethyl-1-butanol (DMB), N,N-dimethylethanolamine (DMEA), N-methylethanolamine (MEA), ethanolamine (EA), trimethylsilyl ethanol, P-choline, a compound from Table 1, and P,P,P-trimethyl ethanolphosphine; or other compounds represented by Formula I. Formula I is as follows: Formula I:

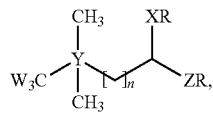

wherein n is an integer, or n is 0, indicating that $CH_2$ is not present;

wherein Y is C, N, Si, P, S, Ge, Sn, Pb, P, As, Sb, or Bi;

wherein each W is independently selected from: H, Cl, F, Br, or I (e.g., $W_3C=CH_3$, $CH_2Cl$, $CH_2Fl$, $CH_2Br$, $CH_2I$, $CF_3$, $CCl_3$, $CBr_3$, $CI_3$, or $CHCl_2$);

wherein X is O or S and the corresponding bond is either present or absent or double, wherein R is absent, H, an alkyl group, alkenyl group, alkynyl group, phenyl group, amide, alkylamide, or a benzyl group;

wherein Z is C, $CH_2$, CH, NH, O or S, wherein XR is alternatively, H, an ester, thioester, or thionester; glycerol, or one of the following three formulas:

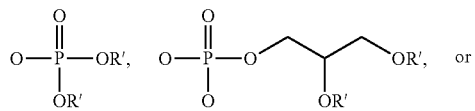

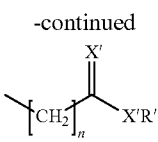

wherein R' is H, an alkyl group, alkenyl group, alkynyl group, phenyl group, or a benzyl group; and wherein X' is O, or S. In certain embodiments, R is amide or alkylamide, and Z is an O, and Z as a double bond O—a carboxylic acid). In some embodiments, the two methyl groups extending from Y are linked by an alkyl or ether to form a 4-6 member ring.

In some embodiments, the first and/or second agent that inhibits the TMA/FMO3/TMAO pathway comprises a compound of Formula I (or N,N-dimethylethanolamine (DMEA), N-methylethanolamine (MEA), ethanolamine (EA), trimethylsilyl ethanol, and P,P,P-trimethyl ethanolphosphine) containing food or beverage. In further embodiments, the composition comprises food or liquid containing a compound of Formula I (or N,N-dimethylethanolamine (DMEA), N-methylethanolamine (MEA), ethanolamine (EA), trimethylsilyl ethanol, and P,P,P-trimethyl ethanolphosphine) selected from the group consisting of but not limited to: olive oil, extra virgin olive oil, grape seed oil, yeast containing food, and red wine. In other embodiments, the composition comprises a compound beneficial for reducing TMAO levels. In certain embodiments, the composition is provided in a pill or capsule (e.g., with a filler or binder). In particular embodiments, the compound of Formula I (e.g., dimethylbutanol) prevent TMA formation from choline or other trimethylamine nutrients (e.g. carnitine, glycerophosphocholine, phosphocholine, phosphatodylcholine) from gut flora, or impairs choline transport. In additional embodiments, the compound of Formula I (or N,N-dimethylethanolamine (DMEA), N-methylethanolamine (MEA), ethanolamine (EA), trimethylsilyl ethanol, P-choline, and P,P,P-trimethyl ethanolphosphine) induces one or more of the following when administered to a subject: reduced trimethyl amine level, reduce total cholesterol level, reduced LDL level, increased HDL level, and reduced triglyceride level.

In some embodiments, Formula I has a formula selected from the group consisting of:

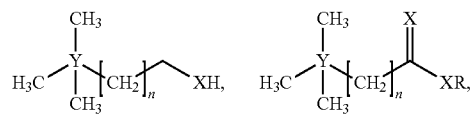

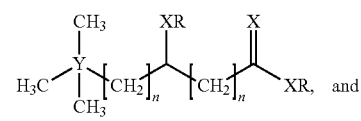

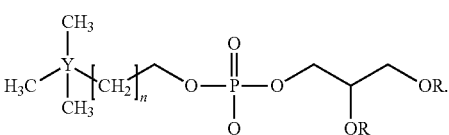

In other embodiments, Formula I has a formula selected from the group consisting of: of:

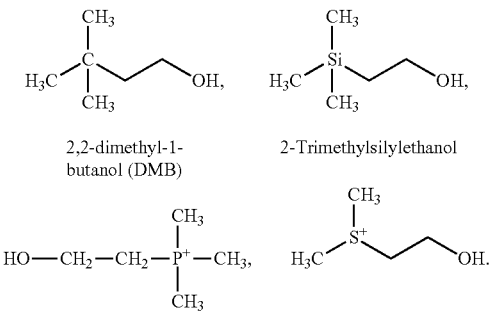

In certain embodiments, Formula I has a formula selected from the group consisting of:

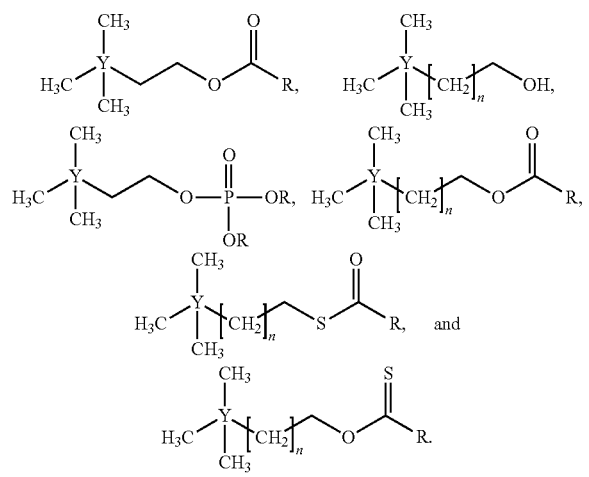

In some embodiments, Formula I has a formula selected from the group consisting of:

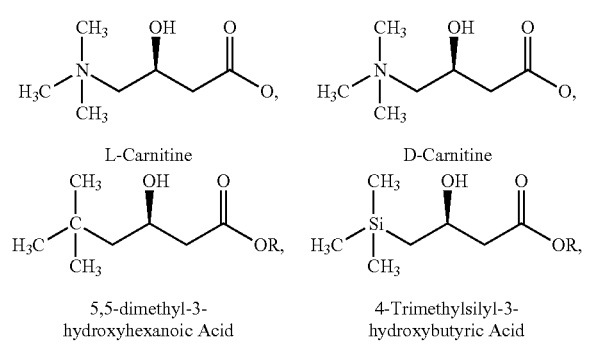

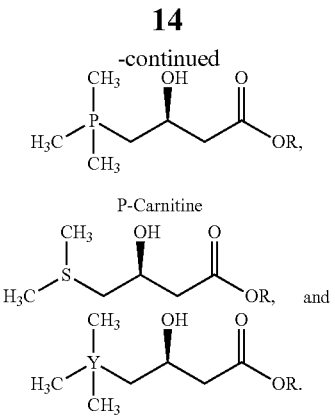

In further embodiments, Formula I has a formula selected from the group consisting of:

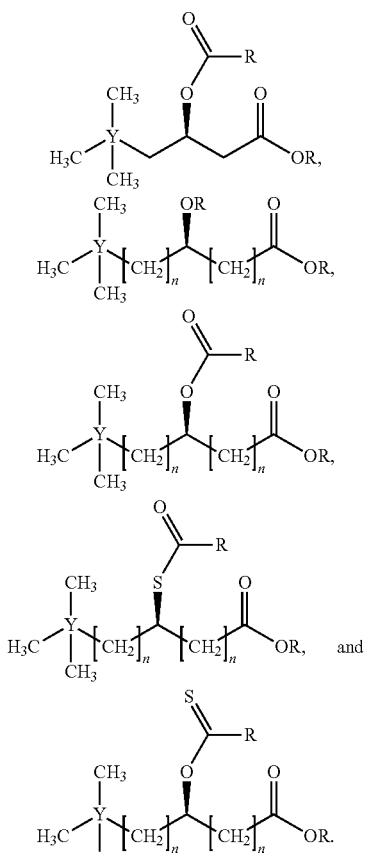

In some embodiments, the compounds of Formula I, or otherwise used in the methods, systems, and compositions here, are those provided in Table 1 below:

TABLE 1

Halomethyl cholines:
(Fluorocholine, Chlorocholine, Bromocholine, Iodocholine)
X = F, Cl, Br, I
Y represents counter ions:
Y = I, Br, Cl

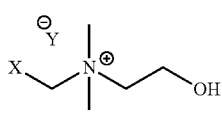

TABLE 1-continued

| | |
|---|---|
| Halomethyl betaines:<br>(Fluorodimethylglycine, Chlorodimethylglycine,<br>Bromodimethylglycine, Iododimethylglycine)<br>X = F, Cl, Br, I | 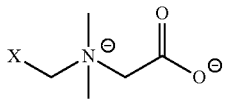 |
| Halomethyl betaine salts:<br>X = F, Cl, Br, I<br>Y represents counter ions:<br>Y = I, Br, Cl | 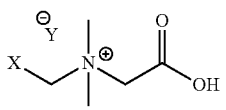 |
| Halomethyl betaine amides:<br>X = F, Cl, Br, I<br>Y represents counter ions:<br>Y = I, Br, Cl | 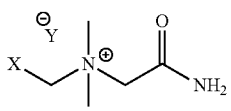 |
| Halomethyl betaine amides:<br>X = F, Cl, Br, I<br>Y = I, Br, Cl<br>R = methyl, ethyl, propyl, amino acids, peptides | 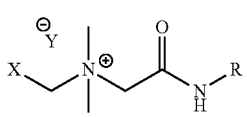 |
| Halomethyl dimethyl amino alcohols:<br>X = F, Cl, Br, I<br>Y = I, Br, Cl<br>R = methyl, ethyl, propyl<br>(e.g. N-Iodomethyl N,N-dimethylamine-2-hydroxy-propanol,<br>when X = I, R = methyl) | 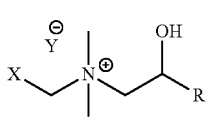 |
| Morpholines:<br>X = H, F, Cl, Br, I<br>Y = Cl, Br, I<br>(e.g. N-methyl-N-(2-hydroxyethyl) morpholine, when X = H) | 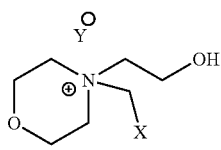 |
| Morpholines:<br>X = H, F, Cl, Br, I<br>Y = Cl, Br, I | 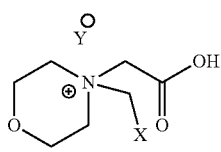 |

III. Methods for Screening Candidate TMAO, FMO3, and TMA Level Lowering Agents In some embodiments, the present invention provides drug screening assays (e.g., to screen for TMAO, FMO3, and/or TMA formation inhibitor drugs). In certain embodiments, the screening methods of the present invention utilize trimethylamine containing precursors (e.g., choline, crotonobetaine (cis and trans), gamma-butyrobetaine, carnitine, 4-Trimethylammoniumbutyraldehyde, dehydrocarnitine, 3-hydroxy-N6-Trimethyl-lysine, N6-Trimethyl-lysine, trimethylammoniumacetone, decarboxycarnitine, phosphocholine, betaine Aldehyde, glycerophosphocholine, phosphatidylcholine, and/or betaine) incubated with intestinal microflora, or a cell-free complex of yeaW/yeaX, capable of cleaving TMA-containing compounds to form TMA. For example, in some embodiments, the present invention provides methods of screening for compounds that inhibit the ability of the microflora from cleaving TMA containing precursors to form TMA or using TMA to form TMAO. In some embodiments, candidate compounds are antibiotic compounds, DMB related compound, antimicrobials, candidate TMA lyase inhibitors (e.g., iodomethyl choline), or candidate FMO3 inhibitors (e.g., from a small molecule library). In some embodiments, such identified agents are employed as the first or second agent herein to treat a subject (e.g., to treat obesity, diabetes, promote weight loss, treat cancer, etc.).

In one screening method, candidate compounds are evaluated for their ability to inhibit TMA formation by microflora or a cell-free complex of yeaW/yeaX by contacting a candidate compound with a sample containing the microflora or a cell-free complex of yeaW/yeaX and TMA containing precursors and then assaying for the effect of the candidate compounds on TMA formation. In some embodiments, the effect of candidate compounds on TMA formation is assayed for by detecting the level of TMA formed.

The test compounds of the present invention can be obtained, for example, using any of the numerous approaches in combinatorial library methods known in the art, including biological libraries; peptoid libraries (libraries of molecules having the functionalities of peptides, but with a novel, non-peptide backbone, which are resistant to enzymatic degradation but which nevertheless remain bioactive; see, e.g., Zuckennann et al., J. Med. Chem. 37: 2678-85 (1994)); spatially addressable parallel solid phase or solution phase libraries; synthetic library methods requiring deconvolution; the 'one-bead one-compound' library method; and synthetic library methods using affinity chromatography selection. The biological library and peptoid library approaches are generally preferred for use with peptide libraries, while the other four approaches are applicable to peptide, non-peptide oligomer or small molecule libraries of compounds (Lam (1997) Anticancer Drug Des. 12:145).

In certain embodiments, the test compounds are antibiotics. Any type of antibiotic may be screened (or used to treat disease). Examples of such antibiotics include, but are not limited to, Ampicillin; Bacampicillin; Carbenicillin Indanyl; Mezlocillin; Piperacillin; Ticarcillin; Amoxicillin-Clavulanic Acid; Ampicillin-Sulbactam; Benzylpenicillin; Cloxacillin; Dicloxacillin; Methicillin; Oxacillin; Penicillin G; Penicillin V; Piperacillin Tazobactam; Ticarcillin Clavulanic Acid; Nafcillin; Cephalosporin I Generation; Cefadroxil; Cefazolin; Cephalexin; Cephalothin; Cephapirin; Cephradine; Cefaclor; Cefamandol; Cefonicid; Cefotetan; Cefoxitin; Cefprozil; Ceftmetazole; Cefuroxime; Loracarbef; Cefdinir; Ceftibuten; Cefoperazone; Cefixime; Cefotaxime; Cefpodoxime proxetil; Ceftazidime; Ceftizoxime; Ceftriaxone; Cefepime; Azithromycin; Clarithromycin; Clindamycin; Dirithromycin; Erythromycin; Lincomycin; Troleandomycin; Cinoxacin; Ciprofloxacin; Enoxacin; Gatifloxacin; Grepafloxacin; Levofloxacin; Lomefloxacin; Moxifloxacin; Nalidixic acid; Norfloxacin; Ofloxacin; Sparfloxacin; Trovafloxacin; Oxolinic acid; Gemifloxacin; Perfloxacin; Imipenem-Cilastatin Meropenem; Aztreonam; Amikacin; Gentamicin; Kanamycin; Neomycin; Netilmicin; Streptomycin; Tobramycin; Paromomycin; Teicoplanin; Vancomycin; Demeclocycline; Doxycycline; Methacycline; Minocycline; Oxytetracycline; Tetracycline; Chlortetracycline; Mafenide; Silver Sulfadiazine; Sulfacetamide; Sulfadiazine; Sulfamethoxazole; Sulfasalazine; Sulfisoxazole; Trimethoprim-Sulfamethoxazole; Sulfamethizole; Rifabutin; Rifampin; Rifapentine; Linezolid; Streptogramins; Quinopristin Dalfopristin; Bacitracin; Chloramphenicol; Fosfomycin; Isoniazid; Methenamine; Metronidazol; Mupirocin; Nitrofurantoin; Nitrofurazone; Novobiocin; Polymyxin; Spectinomycin; Trimethoprim; Colistin; Cycloserine; Capreomycin; Ethionamide; Pyrazinamide; Para-aminosalicyclic acid; and Erythromycin ethylsuccinate.

Examples of methods for the synthesis of molecular libraries can be found in the art, for example in: DeWitt et al., Proc. Natl. Acad. Sci. U.S.A. 90:6909 (1993); Erb et al., Proc. Nad. Acad. Sci. USA 91:11422 (1994); Zuckermann et al., J. Med. Chem. 37:2678 (1994); Cho et al., Science 261:1303 (1993); Carrell et al., Angew. Chem. Int. Ed. Engl. 33.2059 (1994); Carell et al., Angew. Chem. Int. Ed. Engl. 33:2061 (1994); and Gallop et al., J. Med. Chem. 37:1233 (1994). Libraries of compounds may be presented in solution (e.g., Houghten, Biotechniques 13:412-421 (1992)), or on beads (Lam, Nature 354:82-84 (1991)), chips (Fodor, Nature 364:555-556 (1993)), bacteria or spores (U.S. Pat. No. 5,223,409; herein incorporated by reference), plasmids (Cull et al., Proc. Nad. Acad. Sci. USA 89:18651869 (1992)) or on phage (Scott and Smith, Science 249:386-390 (1990); Devlin Science 249:404-406 (1990); Cwirla et al., Proc. Natl. Acad. Sci. 87:6378-6382 (1990); Felici, J. Mol. Biol. 222:301 (1991)).

The ability of the test compound to inhibit TMA formation by intestinal microflora, or a cell-free complex of yeaW/yeaX, can be monitored by detectably labeling the TMA portion of a TMA containing precursor compound. Such detectable labels include, for example, radioisotopes, chromophores, fluorophores, or enzymatic labels. For example, TMA containing precursors can be labeled with $^{125}I$, $^{35}S$ $^{14}C$ or $^3H$, either directly or indirectly, and the radioisotope detected by direct counting of radioemmission or by scintillation counting. Alternatively, TMA containing precursor can be enzymatically labeled with, for example, horseradish peroxidase, alkaline phosphatase, or luciferase, and the enzymatic label detected by determination of conversion of an appropriate substrate to product. In one embodiment, the TMA containing precursor or the test substance is anchored onto a solid phase. The TMA containing precursor anchored on the solid phase can be detected at the end of the reaction.

In certain embodiments, cell free assays can be conducted in a liquid phase using a complex of yeaW/yeaX. In such an assay, the reaction products are separated from unreacted components, by any of a number of standard techniques, including, but not limited to: differential centrifugation (see, for example, Rivas and Minton, Trends Biochem Sci 18:284-7 (1993)); chromatography (gel filtration chromatography, ion-exchange chromatography); electrophoresis (see, e.g., Ausubel et al., eds. Current Protocols in Molecular Biology 1999, J. Wiley: New York.); and immunoprecipitation (see, for example, Ausubel et al., eds. Current Protocols in Molecular Biology 1999, J. Wiley: New York). Such resins and chromatographic techniques are known to one skilled in the art (See e.g., Heegaard J. Mol. Recognit 11:141-8 (1998); Hageand Tweed J. Chromatogr. Biomed. Sci. Appl 699:499-525 (1997)).

This invention further pertains to agents identified by the above-described screening assays. Accordingly, it is within the scope of this invention to further use an agent identified as described herein (e.g., as the first and/or second agent) in an appropriate animal model to determine the efficacy, toxicity, side effects, or mechanism of action, of treatment with such an agent. Furthermore, novel agents identified by the above-described screening assays can be used as the first and/or second agent for treatments as described herein (e.g., to treat a human with obesity, diabetes, etc.).

EXAMPLES

The following example is for purposes of illustration only and are not intended to limit the scope of the claims.

Example 1

Inhibiting the TMA/FMO3/TMAO Pathway

This Examples demonstrates that the gut microbiota-initiated trimethylamine-N-oxide (TMAO)-generating pathway is linked to obesity and energy metabolism. In multiple clinical cohorts, systemic levels of TMAO were observed to strongly associate with type 2 diabetes. In addition, circulating TMAO levels were associated with obesity traits in the different inbred strains represented in the Hybrid Mouse Diversity Panel. Complimentary mouse and human studies indicate a negative regulatory role for FMO3 in the beiging of white adipose tissue. Collectively, this Example reveals a previously unrecognized link between the TMAO-producing enzyme FMO3 and obesity and the beiging of white adipose tissue.

Experimental Procedures

Human Studies

To examine whether circulating choline and TMAO levels were associated with type II diabetes (T2DM) risk, two unique cohorts were recruited, including both men and women with diverse cardiometabolic risk profiles, in cardiology and hepatology clinics at the Cleveland Clinic. These studies were approved by the Cleveland Clinic Institutional Review Board and every subject provided written informed consent. To examine the relationship between FMO3 expression and metabolic traits, this Example took advantage of adipose biopsy microarray data (n=770) within the Metabolic Syndrome in Men (METSIM) study, which has been previously described in detail (Stancakova et al., 2009, herein incorporated by reference in its entirety). The study was approved by the ethics committee of the University of Eastern Finland and Kuopio University Hospital and was conducted in accordance with the Helsinki Declaration. All study participants gave written informed consent. To validate human adipose microarray findings from the METSIM cohort, we analyzed additional microarray data from two distinct cohorts spanning both men and women of European American and African American ethnicity, which have previously been described (Das et al., 2015; Sharma et al., 2016, which are both herein incorporated by reference in their entireties). These studies were approved by the University of Arkansas for Medical Sciences and the Institutional Review Board of Wake Forest School of Medicine. All study participants gave written informed consent. Finally, we examined the protein expression of FMO3 in human liver from normal BMI or bariatric surgery patients. This study was approved by the Institutional Review Board of Wake Forest School of Medicine and all study participants gave written informed consent.

Animal Studies

Because of the known sexual dimorphism of hepatic FMO3 expression in mice, all studies were conducted in adult female mice unless otherwise noted. Mice were maintained on either standard rodent chow (2918 Teklad Global 18% Protein Rodent Diet) or a custom high fat diet comprised of 45% kcal derived from fat (Brown et al., 2010). To establish FMO3 knockout mice, we used CRISPR-Cas9 gene editing. Plasma TMA and TMAO quantification and FMO activity measurements were measured using stable isotope dilution mass spectrometry-based assays as previously described (Wang et al., 2014; Warner et al., 2015) on a Shimadzu 8050 triple quadrupole mass spectrometer. All mice studies were approved by Institutional Animal Care and Use Committees of the Cleveland Clinic, Case Western Reserve University, or University of California—Los Angeles.

Statistical Analysis

To examine the association between circulating choline and TMAO with T2DM, Wilcoxon rank-sum tests were used for continuous variables and $\chi 2$ tests were used for categorical variables. Multilogistic regression models were used to estimate odds ratio and 95% confidence interval for diabetes. All analyses were performed using R 3.1.0 (Vienna, Austria) and p≤0.05 was considered statistically significant. All mouse data were analyzed using either one-way or two-way analysis of variance (ANOVA), where appropriate, followed by post hoc analysis. Differences were considered significant at p≤0.05. All mouse data analyses were performed using JMP Pro 10 (SAS Institute; Cary, N.C.) or GraphPad Prism 6 (La Jolla, Calif.) software.

Results

Elevated Systemic Levels of TMAO are Associated with Type 2 Diabetes in Humans

To first establish clinical relevance, we investigated the relationship of fasting plasma levels of choline or TMAO with type 2 diabetes mellitus (T2DM) risk in two independent cohorts of subjects undergoing elective cardiac risk factor evaluation and recommendations in our preventative cardiology clinic (n=187) or evaluation for suspected non-alcoholic fatty liver disease in our hepatology clinic (n=248). Plasma concentrations of TMAO were significantly higher in subjects with T2DM in each of the individual cohorts, as well as when the cohorts were combined (FIG. 1A). Fasting choline levels were significantly higher only in T2DM subjects from the hepatology cohort (FIG. 1B). Similarly, we observed a dose-dependent association between higher TMAO concentrations and the presence of T2DM (FIG. 1C), while the association between choline and T2DM was seen only in the hepatology cohort (FIG. 1D). After adjustments for multiple comorbidities, prevalent CVD and CVD risk factors, medications, and renal function, TMAO remained a strong predictor of T2DM risk in both cohorts analyzed alone, as well as when the cohorts were combined. Collectively, these data indicate that circulating levels of the meta-organismal metabolite TMAO are closely correlated with T2DM risk in humans.

Plasma TMAO Levels in Mice and FMO3 mRNA Expression in Men Demonstrate Positive Correlations with Obesity First, using a systems genetics approach in mice, we examined various obesity-related traits and circulating TMAO levels in mice from the Hybrid Mouse Diversity Panel (HMDP) fed an obesogenic high fat and high sucrose diet (Parks et al., 2013). Across the different inbred strains represented in the HMDP, circulating levels of TMAO were positively associated with body weight, fat mass, mesenteric adiposity, and subcutaneous adiposity (FIG. 2A-D). Given the observed associations between TMAO and obesity across the diverse inbred strains of mice, we next set out to determine whether expression of FMO3, which encodes the TMAO-producing enzyme, was differentially expressed in the adipose tissue of overweight or obese humans. To do this we first examined a random sampling (n=770) of a large population-based study of Finnish men known as the METSIM study (Stancakova et al., 2009). This study performed dense phenotypic characterization of subjects for characteristics related to adiposity and insulin sensitivity, including adipose biopsies and microarray expression analysis (Stancakova et al., 2009; Civelek et al., 2017). When we examined the correlation between expression levels of all members of the flavin-containing monooxygenase (FMO) family in adipose tissue with metabolic traits in this population, we found that FMO3 was positively correlated with body mass index (BMI) and waist-to-hip ratio, and negatively correlated with the Matsuda Index (Matsuda and DeFronzo, 1999), which is a measure of insulin sensitivity (FIG. 2E). Interestingly, FMO3 mRNA expression levels in human adipose tissue were significantly negatively correlated with several genes that represent selective markers of beige or brown adipocytes that have recently been reported (Wu et al., 2012; Ussar S et al., 2014) (FIG. 2E). These data suggest that FMO3 expression is negatively associated with beiging signatures in human subcutaneous white adipose tissue.

Given that the METSIM study only includes Finnish men, we set out to validate microarray expression data in several distinct cohorts spanning both men and women of European American and African American ethnicity. Importantly, these validation cohorts were also chosen for their gender, ethnic and racial diversity, and because each has been extensively characterized for obesity and cardiometabolic phenotypes (Das et al., 2015; Sharma et al., 2016). The first cohort included n=99 non-Hispanic Caucasian Americans, comprised of 42 males and 57 females (Das et al., 2015). The second cohort included n=260 African Americans, comprised of 139 males and 121 females (Sharma et al., 2016). In agreement with findings from the METSIM study (FIG. 2E), we found that FMO3 was positively correlated with BMI and adiposity, and negatively correlated with insulin sensitivity in both European American and African American men and women. Also, the primary transcript variant of FMO3 was negatively correlated with the beige/brown marker genes uncoupling protein 1 (UCP1) and PR domain-containing 16 (PRDM16).

In further studies, we sought to examine whether similar associations were observed between FMO3 expression in human liver and metabolic traits using liver biopsies from obese patients undergoing bariatric surgery and normal weight controls. In contrast to our findings in human adipose tissue (FIG. 2E), we did not find significant correlations between liver FMO3 protein levels and metabolic traits in this cohort. Of note, the protein expression of FMO3 in human liver does not significantly differ between males and females in the cohort under study (n=15 males, n=35 females; p=0.79).

Genetic Deletion of the TMAO-Producing Enzyme FMO3 Protects Mice from Obesity

Figure 3:
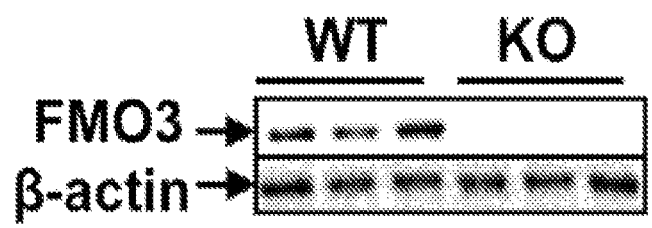
FIG. 3 shows genetic deletion of FMO3 protects mice from diet-induced obesity.
Figure 3:
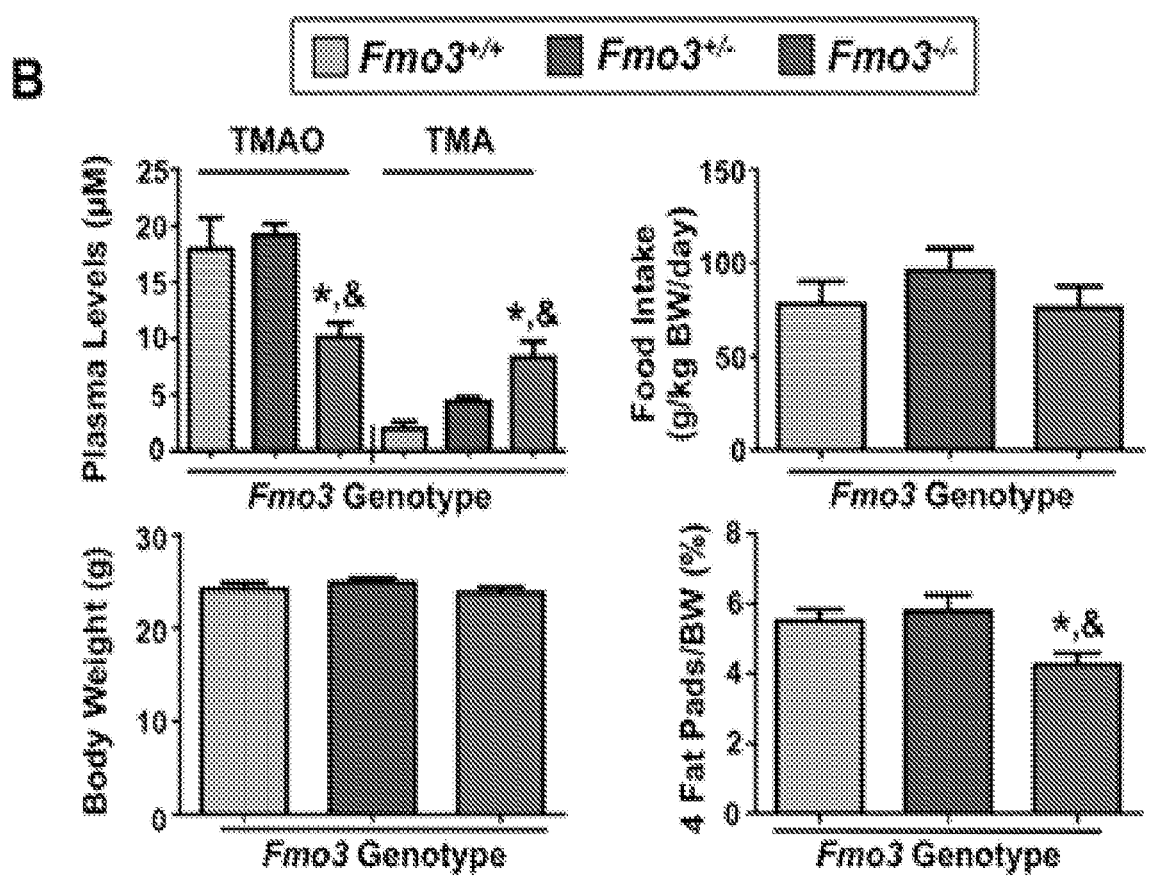
Figure 3:
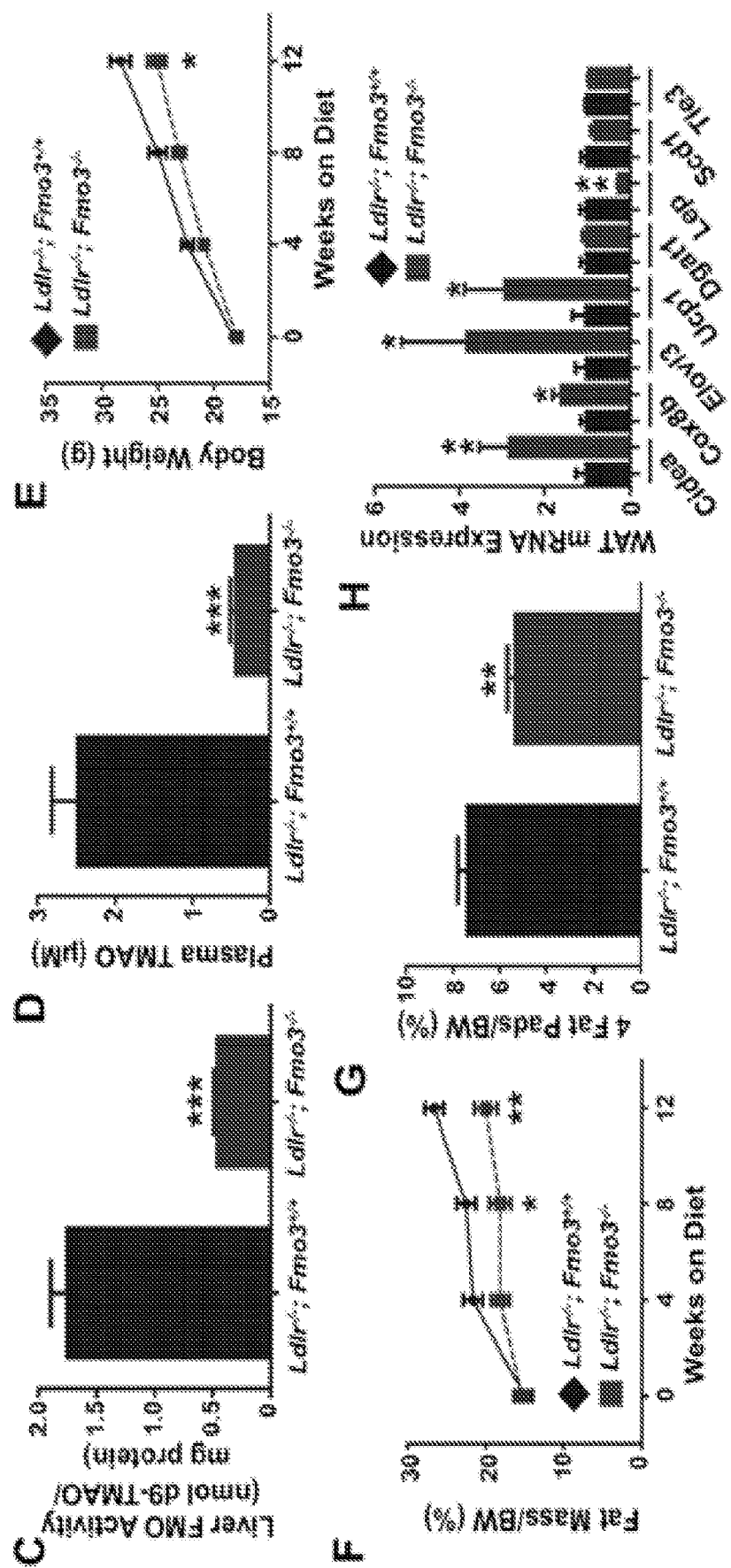

To further examine the role of FMO3 in obesity, we examined global FMO3 knockout (Fmo3−/−) mice generated using CRISPR-Cas9-mediated gene editing (Shih, et al., in preparation) (FIG. 3). Hepatic FMO3 protein was undetectable by Western blot in Fmo3−/− mice (FIG. 3A). In initial studies, we maintained Fmo3−/− mice on a C57BL/6 background and fed a choline-supplemented chow-based diet. Under these non-obesogenic conditions, Fmo3−/− mice accumulate plasma TMA and have diminished TMAO as predicted, and while there were no differences in food intake or body weight, they do exhibit significantly reduced adiposity compared to Fmo3+/+ mice (FIG. 3B). To examine effects of FMO3 knockout on adiposity under obesogenic conditions we crossed Fmo3−/− mice to the low-density lipoprotein knockout (Ldlr−/−) background and maintained mice on a Western diet (FIG. 3C-5H). Western diet-fed Ldlr−/−; Fmo3−/− mice had markedly reduced hepatic FMO activity (FIG. 3C) and circulating TMAO levels (FIG. 3D), when compared to Ldlr−/−; Fmo3+/+ control mice. Western diet-fed Ldlr−/−; Fmo3−/− mice were protected against diet-induced obesity (FIG. 3E-G), and had increased expression of brown/beige adipocyte marker genes in the subcutaneous fat depots compared to Ldlr−/−; Fmo3+/+ control mice (FIG. 3H). Collectively, these data provide genetic evidence that FMO3 is a negative regulator of beiging programs in white adipose tissue.

Important findings of this Example include, for example: (1) circulating levels of the gut microbe-derived metabolite TMAO are associated with enhanced risk of T2DM in humans; (2) TMAO levels are associated with adiposity traits across mouse strains within the Hybrid Mouse Diversity Panel; (3) adipose tissue expression of FMO3 is positively associated with obesity in humans; (4) FMO3 mRNA expression is negatively associated with brown/beige adipocyte gene expression in white adipose tissue in humans; (5) FMO3 genetic deletion protects mice against high fat diet-induced obesity; and (6) FMO3 genetic deletion is associated with the beiging of white adipose tissue in mice.

While the present invention is not limited to any particular mechanism, and an understanding of the mechanism is not necessary to practice the invention it is believed, based on the present example, that it appears that the phenotypic effects of FMO3 deletion could be driven by a combination of factors including: (1) chronic increases in the levels of TMA, (2) chronic decreases in the levels of TMAO, and/or (3) effects driven by other FMO3 substrates or products. Such findings support a model where TMAO may be involved in specific transcriptional reprogramming in adipocytes. TMA is known to activate the G protein-coupled receptor trace amine-associated receptor 5 (TAAR5); however, TAAR5 does not recognize TMAO (Li et al., 2013).

In conclusion, this Example highlights a role for the TMA/FMO3/TMAO meta-organismal pathway in the progression of disease such as obesity-related disorders. Given the numerous strong associations of the gut microbe-driven TMAO pathway with human disease, this work has broad implications for disease treatment and drug discovery efforts targeting gut microbes themselves instead of the human host in which they reside.

Example 2

TMA Lyase Inhibition

This Examples demonstrates that impact of TMA lyase inhibition using iodomethyl choline (IMC).

6-week-old male C57BL6/J mice were maintained on either 60% high fat diet (HFD) or HFD supplemented with 0.06% TMA lyase inhibitor iodomethyl choline (HFD+IMC) for weeks. Results are shown in FIG. 7 (A-E): A) Plasma TMA and TMAO levels (uM); B) Body weight (g); C) Food consumption normalized to body weight (g of diet consumed per day per g of body weight); D) Glucose tolerance measured after 12 weeks on diet; and E) Plasma insulin measured following an overnight fast (Fasted) or 4 hours postprandially (Fed); n=4-5 mice/group. This work demonstrated that TMA lyase inhibition improves obesity driven by high fat diet or leptin deficiency.

6-week-old male leptin deficient ob/ob mice were maintained on either control diet (Con) or control diet supplemented with 0.06% TMA lyase inhibitor iodomethyl choline (Con+IMC) for 16 weeks. Results are shown in FIG. 7(F-J): F) Plasma TMA and TMAO levels (uM); G) Body weight (g); H) Food consumption normalized to body weight (g of diet consumed per day per g of body weight); I) Glucose tolerance measured after 12 weeks on diet; and J) Mean oxygen consumption (VO2; ml/kg/hr) measured after 5 weeks on diet; n=6 mice/group.

To determine the role of TMA and TMAO on diet-induced obesity, cohorts of 6-week-old male C57BL6/J mice fed HFD and HFD+IMC were supplemented with either 100 mM TMA in the drinking water (K-M) or 0.3% w/w TMAO in the diet (N-P). HFD and HFD+IMC data in panels N-P are the same as those depicted in A, B, and D above and have been replicated here for comparison. FIGS. 7K-P specifically show: K) Plasma TMA and TMAO levels (uM) after 6 weeks on diet and TMA supplementation; L) Body weight (g) over 12 weeks; M) Glucose tolerance measured after 10 weeks on diet and TMA supplementation; N) Plasma TMA and TMAO levels (uM) after 12 weeks on diet and TMAO supplementation; O) Body weight (g) over 20 weeks; and P) Glucose tolerance measured after 12 weeks on diet and TMAO supplementation. n=8-10 mice per diet group for all studies unless otherwise indicated. Data represented as mean+/−SEM. Statistical significance determined using student's t-test or two-way ANOVA where appropriate.

IMC alters the cecum microbiota composition in models of high fat diet-induced and leptin deficient obesity. FIG. 8A-F represents data from HFD model and G-K the Ob/Ob model. FIG. 8A,G. Principal co-ordinate analysis (PCoA) plot of microbiota profiles built from weighted Unifrac distances. Each point represents a single sample from a single mouse. Positions of points in space display dissimilarities in the microbiota, with points further from one another being more dissimilar. FIG. 8B,H. Barplot of cecal microbiota at the phylum level. Each bar represents an individual mouse and each color an individual phyla. FIG. 8C. Relative abundance of Firmicutes, Bacteroidetes and the Firmicutes to Baceteroidetes ratio for mice on HFD with or without IMC. The boxes represent the 25th and 75th quartiles, and the line displays the median value within each group. Points extending beyond the lines are outliers defined as values greater or less than 1.5 times the interquartile range. FIG. 8D,I. Linear discriminatory analyses (LDA) plot of taxa differing significantly with IMC. FIG. 8E,J. Spearman's correlation between Akkermansia muciniphila and TMA/body weight. Values in both X and Y directions are plotting as mean±SEM. F,K. Representative OTUs that correlate with body weight, TMA and insulin in both the HFD and Ob/Ob models.

IMC alters the cecum microbiota composition in models of high fat diet-induced and leptin deficient obesity. FIG. 8A-F represents data from HFD model and G-K the Ob/Ob model. FIG. 8A,G. Principal co-ordinate analysis (PCoA) plot of microbiota profiles built from weighted Unifrac distances. Each point represents a single sample from a single mouse. Positions of points in space display dissimilarities in the microbiota, with points further from one another being more dissimilar. FIG. 8B,H. Barplot of cecal microbiota at the phylum level. Each bar represents an individual mouse and each color an individual phyla. FIG. 8D,I. Linear discriminatory analyses (LDA) plot of taxa differing significantly with IMC. E,J. Spearman's correlation between Akkermansia muciniphila and TMA/body weight. Values in both X and Y directions are plotting as mean±SEM. F,K. Representative OTUs that correlate with body weight, TMA and insulin in both the HFD and Ob/Ob models.

REFERENCES

Bäckhed, et al., (2004). The gut microbiota as an environmental factor that regulates fat storage. Proc Natl Acad Sci USA 101, 15718-15723.

Bartell, A., and Heeren J. (2014). Adipose tissue browning and metabolic health. Nat Rev Endocrinol. 10, 24-36.

Bennett, et al. (2013). Trimethylamine-N-oxide, a metabolite associated with atherosclerosis, exhibits complex genetic and dietary regulation. Cell Metab 17, 49-60.

Brown, J. M., and Hazen, S. L. (2015). The gut microbial endocrine organ: bacterially derived signals driving cardiometabolic diseases. Annu. Rev. Med. 66, 343-359.

Cashman J. R., and Zhang, J. (2006). Human flavin-containing monooxygenases. Annu. Rev. Pharmacol. Toxicol. 46, 65-100.

Civelek, et al. (2017). Genetic regulation of adipose gene expression and cardio-metabolic traits. Am. J. Human Genet. 100, 428-443.

Cox, et al. (2014). Altering the intestinal microbiota during a critical development window has lasting metabolic consequences. Cell 158, 705-721.

Dambrova et al., (2016). Diabetes is associated with higher trimethylamine N-oxide plasma levels. Exp. Clin. Endocrinol. Diabetes 124, 251-256.

Das et al., (2015). Integrative network analysis reveals different pathophysiological mechanisms of insulin resistance among Caucasians and African Americans. BMC Med. Genomics 8, 4.

Gao et al., (2014). Dietary trimethylamine-N-oxide exacerbates impaired glucose tolerance in mice fed a high fat diet. J. Biosci. Bioeng. 118, 476-81.

Gregory et al. (2015). Transmission of Atherosclerosis Susceptibility with Gut Microbial Transplantation. J Biol Chem. 290, 5647-5660.

Jiang et al., (2012). Maternal choline intake alters the epigenetic state of fetal cortisol-regulating genes in humans. FASEB J. 26, 3563-3574.

Koeth et al. (2013). Intestinal microbiota metabolism of L-carnitine, a nutrient in red meat, promotes atherosclerosis. Nat Med 19, 576-585.

Koeth et al. (2014). γ-Butyrobetaine is a proatherogenic intermediate in gut microbial metabolism of L-carnitine to TMAO. Cell Metab 20, 799-812.

Ley et al., (2005). Obesity alters gut microbial ecology. Proc. Natl. Acad. Sci. USA 102, 11070-11075.

Lever et al., (2014). Betaine and trimethylamine-N-oxide as predictors of cardiovascular outcomes show different patterns in diabetes mellitus: an observational study. PLoS One 9, e114969.

Li et al. (2013). Synchronous evolution of an odor biosynthesis pathway and behavioral response. Curr. Biol. 23, 11-20.

Mafune et al., (2016). Associations among serum trimethylamine-N-oxide (TMAO) levels, kidney function and infarcted coronary artery number in patients undergoing cardiovascular surgery: a cross-sectional study. Clin Exp Nephrol. 20, 731-739.

Matsuda, M., and DeFronzo, R. (1999). Insulin sensitivity indices obtained from oral glucose tolerance testing: comparison with the euglycemic insulin clamp. Diabetes Care 22, 1462-1470.

Missailidis et al., (2016). Serum Trimethylamine-N-Oxide Is Strongly Related to Renal Function and Predicts Outcome in Chronic Kidney Disease. PLoS One 11, e0141738.

Miao et al., Morbid Obesity Study Group, et al. (2015). Flavin-containing monooxygenase 3 as a potential player in diabetes-associated atherosclerosis. Nat Commun 6, 6498.

Muoio, D. M. (2014). Metabolic inflexibility: when mitochondrial indecision leads to metabolic gridlock. Cell 159, 1253-1262.

Parks et al. (2013). Genetic control of obesity and gut microbiota composition in response to high-fat, high-sucrose diet in mice. Cell Metab. 17, 141-152.

Poly et al., (2011). The relation of dietary choline to cognitive performance and white-matter hyperintesity in the Framingham Offspring Cohort. Am. J. Clin. Nutr. 94, 1584-1591.

Puigserver et al; (1998). A cold-inducible coactivator of nuclear receptors linked to adaptive thermogenesis. Cell 92, 829-839.

Romano et al., (2015). Intestinal microbiota composition modulates choline bioavailability from diet and accumulation of the proatherogenic metabolite trimethylamine-N-oxide. mBio 6, e02481-14.

Sharma et al. (2016). Tissue-specific and genetic regulation of insulin sensitivity-associated transcripts in African Americans. J. Clin. Endocrinol. Metab. 101, 1455-1468.

Shaw et al., (2009). Choline and risk of neural tube defects in a folate-fortified population. Epidemiology 20, 714-719.

Shih et al. (2015). Flavin containing monooxygenase 3 exerts broad effects on glucose and lipid metabolism and atherosclerosis. J Lipid Res 56, 22-37.

Stancakova et al., (2009). Association of 18 confirmed susceptibility loci for type 2 diabetes with indices of insulin release, proinsulin conversion, and insulin sensitivity in 5,327 nondiabetic Finnish men. Diabetes 58, 2129-2136.

Suzuki et al., (2016). Trimethylamine N-oxide and prognosis in acute heart failure. Heart. 102, 841-848.

Tang et al., (2013). Intestinal microbial metabolism of phosphatidylcholine and cardiovascular risk. N Engl J Med 368, 1575-1584.

Tang et al., (2014). Prognostic value of elevated levels of intestinal microbe-generated metabolite trimethylamine-N-oxide in patients with heart failure: refining the gut hypothesis. J Am Coll Cardiol 64, 1908-1914.

Tang et al., (2017). Increased trimethylamine N-oxide portends high mortality risk independent of glycemic control in patients with type 2 diabetes mellitus. Clin. Chem. 63, 297-306.

Thomas et al. (2013). The serine hydrolase ABHD6 is a critical regulator of the metabolic syndrome. Cell Rep. 5, 508-520.

Trøseid et al. (2015). Microbiota-dependent metabolite trimethylamine-N-oxide is associated with disease severity and survival of patients with chronic heart failure. J Intern Med. 277, 717-726.

Turnbaugh, P. J., and Gordon, J. I. (2009). The core gut microbiome, energy balance and obesity. J. Physiol. 587, 4153-4158.

Ussar et al. (2014). ASC-1, PAT2, and P2RX5 are cell surface markers for white, beige, and brown adipocytes. Sci. Transl. Med. 6, 247re103.

Wang et al. (2011). Gut flora metabolism of phosphatidylcholine promotes cardiovascular disease. Nature 472, 57-63.

Wang et al., (2014). Prognostic value of choline and betaine depends on intestinal microbiota-generated metabolite trimethylamine-N-oxide. Eur Heart J 35, 904-910.

Wang et al. (2015). Non-lethal inhibition of gut microbial trimethylamine production for the treatment of atherosclerosis. Cell 163, 1585-1595.

Warrier et al. (2015). The TMAO-Generating Enzyme Flavin Monooxygenase 3 Is a Central Regulator of Cholesterol Balance. Cell Rep 10, 1-13.

Wu et al. (2012). Beige adipocytes are a distinct type of thermogenic fat cell in mouse and human. Cell 150, 366-376.

Zhu et al. (2016). Gut microbial metabolite TMAO enhances platelet hyperreactivity and thrombosis risk. Cell 165, 111-124.

Although only a few exemplary embodiments have been described in detail, those skilled in the art will readily appreciate that many modifications are possible in the exemplary embodiments without materially departing from the novel teachings and advantages of this disclosure. Accordingly, all such modifications and alternative are intended to be included within the scope of the invention as defined in the following claims. Those skilled in the art should also realize that such modifications and equivalent constructions or methods do not depart from the spirit and scope of the present disclosure, and that they may make various changes, substitutions, and alterations herein without departing from the spirit and scope of the present disclosure.

What is claimed is:

1. A method of treating a disease or condition or causing weight loss comprising: treating a human subject, that has been identified as having elevated levels of trimethylamine (TMA), trimethylamine N-oxide (TMAO), or flavin monooxygenase 3 (FMO3) mRNA, with:
   a) a first agent or first procedure that inhibits the TMA/FMO3/TMAO pathway to cause weight loss, and/or treat a first disease or first condition, or
   b) a second agent or second procedure that is a non-antibiotic that inhibits said TMA/FMO3/TMAO pathway to treat a second disease or second condition,
   wherein said first disease or first condition is selected from the group consisting of: obesity, dyslipidemia, arthritis pain, sleep apnea, diabetes-associated neuropathy, diabetes-associated cardiovascular disease, diabetes-associated cerebrovascular disease, diabetes-associated peripheral vascular disease, diabetes-associated retinopathy, diabetes-associated nephropathy, diabetes-associated ulceration, colorectal cancer, hepatocellular carcinoma, clear cell renal carcinoma, alcoholic steatohepatitis (ASH), alcoholic cirrhosis, Hepatitis C Virus driven (HCV-driven) liver fibrosis, Hepatitis B Virus driven (HBV-driven) liver fibrosis, primary sclerosing cholangitis (PSC), biliary atresia, gall stones, cholestasis, Cushing syndrome, impaired glucose tolerance, prediabetes, hyperglycemia, elevated insulin state, weight management, and arterial aneurysms,
   wherein said second disease or second condition is selected from the group consisting of:
   diabetes mellitus, insulin resistance, metabolic syndrome, nonalcoholic fatty liver disease (NAFD), and nonalcoholic steatohepatitis (NASH), and
   wherein said first agent or procedure and/or said second agent or procedure is selected from the group consisting of:
   i) 3,3-dimethyl-1-butanol (DMB) or a DMB derivative or related compound;
   ii) acetylsalicylic acid with or without an enteric coating;
   iii) an acetylsalicylic acid derivative with or without an enteric coating;
   iv) a flavin monooxygenase 3 (FMO3) inhibitor;
   v) a gut TMA lyase inhibitor;
   vi) fecal microbiota transplantation;
   vii) delivery of acetylsalicylic acid or derivative thereof directly to the colon or cecum of said subject;
   viii) an antiplatelet agent;
   ix) a TMA and/or TMAO sequestering agent;
   x) a moiety from Table 1 selected from the group consisting of: i) a halomethyl choline, ii) a halomethyl betaine, iii) a halomethyl betaine salt, iv) a halomethyl betaine amide, and iv) a halomethyl dimethyl amine alcohol;
   xi) a compound comprising at least one of: N,N-dimethylethanolamine (DMEA), N-methylethanolamine (MEA), ethanolamine (EA), trimethylsilyl ethanol, P-choline, and P,P,P-trimethyl ethanolphosphine; and
   xii) an agent that inhibits trimethylamine-induced human trace amine-associated receptor 5 (TAAR5) activation.

2. The method of claim 1, wherein said subject is treated with said first agent, wherein said first agent comprises said DMB derivative or related compound, and wherein said DMB derivative or related compound is as shown in Formula I below:

$$W_3C-\underset{\underset{CH_3}{|}}{\overset{\overset{CH_3}{|}}{Y}}-[CH_2]_n-\overset{XR}{\underset{}{\underset{}{C}}}-ZR,$$

wherein n is an integer, or n is 0, indicating that $CH_2$ is not present;
wherein Y is C, N, Si, P, S, Ge, Sn, Pb, P, As, Sb, or Bi;
wherein each W is independently selected from: H, Cl, F, Br, or I;
wherein X is O, or S, and the corresponding bond is either present or absent or double,
wherein R is absent, H, an alkyl group, alkenyl group, alkynyl group, phenyl group, amide, alkylamide, or a benzyl group;
wherein Z is C, $CH_2$, CH, O, NH, or S,
wherein XR is, alternatively, H, an ester, thioester, or thionester; glycerol, or one of the following three formulas:

$$O-\overset{\overset{O}{||}}{\underset{\underset{OR'}{|}}{P}}-OR', \quad O-\overset{\overset{O}{||}}{\underset{\underset{O}{|}}{P}}-O\diagup\diagdown\underset{OR'}{\diagup}\diagdown OR', \quad or$$

$$[CH_2]_n\overset{X'}{\underset{}{\diagup\diagdown}}X'R';$$

wherein R' is H, an alkyl group, alkenyl group, alkynyl group, phenyl group, or a benzyl group; and
wherein X' is O, or S.

3. The method of claim 1, wherein said subject is treated with said first agent, wherein said first agent comprises said acetylsalicylic acid derivative, and wherein said acetylsalicylic acid derivative is 5-aminosalysillic acid.

4. The method of claim 1, wherein said subject is treated with said first agent, wherein said first agent comprises said FMO3 inhibitor, and wherein said FMO3 inhibitor comprises Tenofovir, Methimazole, an anti-FMO3 monoclonal antibody or antigen-binding portion thereof, or anti-FMO3 siRNA or shRNA.

5. The method of claim 1, wherein said subject is treated with said first agent, wherein said first agent comprises said antiplatelet agent, and wherein said antiplatelet agent is selected from the group consisting of: abciximab, dipyridamole/ASA, anagrelide, cilostazol, clopidogrel, dipyridamole, eptifabatide, prasugrel, ticagrelor, ticlopidine, tirofiban, and vorapaxar.

6. The method of claim 1, wherein said subject is treated with said first agent, wherein said first agent comprises said acetylsalicylic acid or acetylsalicylic acid derivative with an enteric coating, and wherein said enteric coating provides for release of a majority of said acetylsalicylic acid or said acetylsalicylic acid derivative in the colon or cecum of said subject.

7. The method of claim 1, wherein said subject is treated with said first agent, and wherein said first agent comprises said halomethyl choline.

8. The method of claim 7, wherein said halomethyl choline comprises fluorocholine.

9. The method of claim 1, wherein said first disease or first condition is obesity.

10. The method of claim 1, wherein said second disease or second condition is said diabetes mellitus.

11. The method of claim 1, wherein said second disease or second condition is said insulin resistance.

12. The method of claim 1, wherein said second disease or second condition is said metabolic syndrome.

13. The method of claim 1, wherein said second disease or second condition is said nonalcoholic fatty liver disease (NAFD).

14. The method of claim 1, wherein said second disease or second condition is said nonalcoholic steatohepatitis (NASH).

15. The method of claim 1, wherein said first agent or first procedure causes said weight loss.

16. A method of treating a disease or condition comprising:
treating a human subject, that has been identified as having elevated levels of trimethylamine (TMA), trimethylamine N-oxide (TMAO), or flavin monooxygenase 3 (FMO3) mRNA, with an agent or procedure that inhibits the TMA/FMO3/TMAO pathway to treat a disease or condition,
wherein said disease or condition is selected from the group consisting of: diabetes mellitus, obesity, insulin resistance, metabolic syndrome, nonalcoholic fatty liver disease (NAFD), and nonalcoholic steatohepatitis (NASH), and
wherein said agent or procedure is selected from the group consisting of:
i) 3,3-dimethyl-1-butanol (DMB) or a DMB derivative;
ii) acetylsalicylic acid with or without an enteric coating;
iii) an acetylsalicylic acid derivative with or without an enteric coating;
iv) a flavin monooxygenase 3 (FMO3) inhibitor;
v) a gut TMA lyase inhibitor;
vi) fecal microbiota transplantation;
vii) delivery of acetylsalicylic acid or derivative thereof directly to the colon or cecum of said subject;
viii) an antiplatelet agent;
ix) a TMA and/or TMAO sequestering agent;
x) a moiety from Table 1 selected from the group consisting of: i) a halomethyl choline, ii) a halomethyl betaine, iii) a halomethyl betaine salt, iv) a halomethyl betaine amide, and iv) a halomethyl dimethyl amine alcohol;
xi) a compound comprising at least one of: N,N-dimethylethanolamine (DMEA), N-methylethanolamine (MEA), ethanolamine (EA), trimethylsilyl ethanol, P-choline, and P,P,P-trimethyl ethanolphosphine; and
xii) an agent that inhibits trimethylamine-induced human trace amine-associated receptor 5 (TAAR5) activation.

17. The method of claim 16, wherein said agent comprises said halomethyl choline.

18. The method of claim 17, wherein said halomethyl choline comprises fluorocholine.

19. The method of claim 17, wherein said halomethyl choline comprises iodocholine.

20. The method of claim 16, wherein said disease or condition treated is obesity.

* * * * *